United States Patent [19]

Muchowski et al.

[11] Patent Number: 4,505,927

[45] Date of Patent: Mar. 19, 1985

[54] 5-BENZOYL-1,2-DIHYDRO-3H-PYR-ROLO[1,2-A]PYRROLE-1-CARBOXYLIC ACIDS AND PHARMACEUTICAL USE THEREOF

[75] Inventors: Joseph M. Muchowski, Sunnyvale, Calif.; Robert Greenhouse, Los Reyes, Mexico

[73] Assignee: Syntex (U.S.A.) Inc., Palo Alto, Calif.

[21] Appl. No.: 339,813

[22] Filed: Jan. 15, 1982

Related U.S. Application Data

[62] Division of Ser. No. 198,551, Oct. 20, 1980, Pat. No. 4,347,189.

[51] Int. Cl.$^3$ .................. C07D 487/06; A61K 31/40
[52] U.S. Cl. ................................ 514/413; 548/453
[58] Field of Search ................. 548/453; 424/274

[56] References Cited

U.S. PATENT DOCUMENTS 4,232,038  11/1980  Kluge et al. .................. 548/453

*Primary Examiner*—Glennon H. Hollrah
*Assistant Examiner*—David B. Springer
*Attorney, Agent, or Firm*—Ellen J. Buckles; Tom M. Moran; Alan M. Krubiner

[57] ABSTRACT

5-benzoyl-7-halo-1,2-dihydro-3H-pyrrolo[1,2-a]-pyrrole-1-carboxylic acids, represented by the formula

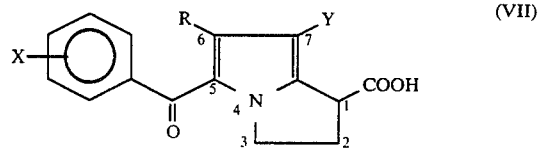

(VII)

and the pharmaceutically acceptable non-toxic esters and salts thereof, wherein:

R is hydrogen or lower alkyl;
X is hydrogen, lower alkyl, lower alkoxyl, lower alkoxycarbonyl, carboxyl, lower alkylcarbonyl, sulfonic acid, sulfonic acid alkyl ester, fluoro, chloro, or bromo; and Y is chloro or bromo, which are novel, and 5-benzoyl-1,2-dihydro-3H-pyrrolo[1,2-a]pyrrole-1-carboxylic acids which are represented by the formula

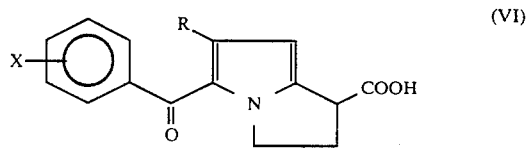

(VI)

wherein X and R are as above defined except that X cannot be chloro or bromo, are prepared by decarboxylation of the corresponding 1,1 dicarboxylates. Intermediates in said preparation are also disclosed.

3 Claims, No Drawings

5-BENZOYL-1,2-DIHYDRO-3H-PYRROLO[1,2-A]PYRROLE-1-CARBOXYLIC ACIDS AND PHARMACEUTICAL USE THEREOF

This is a division of application Ser. No. 198,551 filed Oct. 20, 1980, now U.S. Pat. No. 4,347,189.

BACKGROUND OF THE INVENTION

1. Field of the Invention

The invention herein concerns novel 5-benzoyl-7-halo-1,2-dihydro-3H-pyrrolo[1,2-a]pyrrole-1-carboxylic acids and the pharmaceutically acceptable, non-toxic esters and salts thereof which are useful in the treatment of inflammation, pain and/or pyrexia in mammals, as platelet aggregation inhibitors and fibrinolytic agents, and as smooth muscle relaxants.

Said compounds and the corresponding 5-benzoyl-1,2-dihydro-3H-pyrrolo[1,2-a]pyrrole-1-carboxylic acids are prepared by decarboxylation of the respective corresponding 1,1 dicarboxylates.

Some of the 5-benzoyl-1,2-dihydro-3H-pyrrolo-[1,2-a]pyrrole-1-carboxylic acids, further discussed hereinbelow, and which are prepared by the process described herein, are similarly useful and are novel.

2. Prior Art

5-Benzoyl-1,2-dihydro-3H-pyrrolo[1,2-a]pyrrole-1-carboxylic acids, and their preparation by a synthetic route different from that disclosed herein, have been described in U.S. Pat. No. 4,089,969 and in U.S. application Ser. Nos. 71,443 and 71,444, both filed Aug. 31, 1979. In these compounds, the benzoyl moiety is optionally substituted with lower alkyl, lower alkoxyl, fluoro, chloro or bromo or with alkylthio or alkylsulfinyl. Related 5-aroyl-1,2-dihydro-3H-pyrrolo-[1,2-a]pyrrole-1-carboxylic acids and their pharmaceutically acceptable non-toxic esters and salts are described in U.S. Pat. Nos. 4,087,539 and 4,097,579. The corresponding 1-cyano compounds are described in U.S. Pat. No. 4,140,698. The corresponding 6-halo compounds are described in U.S. application Ser. No. 157,719 filed June 9, 1980.

SUMMARY OF THE INVENTION

The present invention relates to compounds represented by the formula

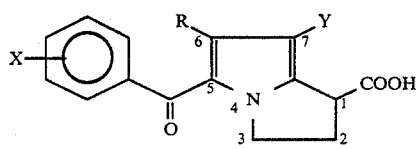

(VII)

and the pharmaceutically acceptable non-toxic esters and salts thereof wherein:

R is hydrogen or lower alkyl;

X is hydrogen, lower alkyl, lower alkoxyl, lower alkoxycarbonyl, carboxyl, lower alkyl carbonyl, sulfonic acid, sulfonic acid alkyl ester, fluoro, chloro or bromo; and Y is chloro or bromo.

X may be at any available position of the benzene ring—ortho, meta or para to the carbonyl.

In another aspect, the invention concerns novel compounds of the formula

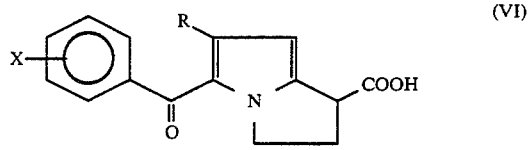

(VI)

and the pharmaceutically acceptable non-toxic esters and salts thereof, wherein R is as defined previously, and X is lower alkoxycarbonyl, carboxyl, lower alkylcarbonyl, sulfonic acid, or sulfonic acid alkyl ester.

Compounds of formula VII and the above described compounds of formula VI and their esters and salts are useful as antiinflammatory, analgesic and anti-pyretic agents, as platelet aggregation inhibitors and fibrinolytic agents, and as smooth muscle relaxants. Accordingly, two other aspects of the invention relate to pharmaceutical compositions containing said compounds and to methods of use of said compounds.

Still another aspect of the present invention concerns a process for the preparation of the compounds of formula VII and their esters and salts. The same process may be applied to the preparation of compounds of the formula

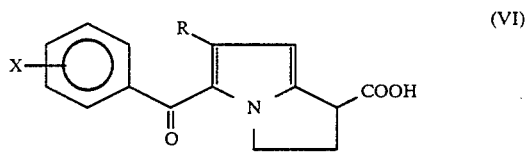

(VI)

wherein R and X are as defined in describing the formula VII, except that X cannot be chloro or bromo. Accordingly another aspect of the invention relates to a process for the preparation of compounds of formula VI and their esters and salts from the corresponding 1,1-dicarboxylates.

Several intermediates, discussed more fully hereinafter, and represented by formulas II, III, IV and V, in the process disclosed herein are novel. Therefore, still another aspect of the present invention relates to them as useful intermediates for synthesis of the compounds of formulas VI and VII.

DETAILED DESCRIPTION

Definitions:

As used herein:

"Pharmaceutically acceptable, non-toxic esters and salts" refers to "alkyl esters" derived from hydrocarbons of branched or straight chain, having from one to 12 carbon atoms and to "glycerylesters" which consist of glycerol esterified both to the compound herein and to fatty acids; and to salts derived from pharmaceutically acceptable non-toxic inorganic and organic bases, respectively.

Typical alkyl ester groups are, for example, methyl, ethyl, propyl, isopropyl, butyl, t-butyl, isoamyl, pentyl; isopentyl, hexyl, octyl, nonyl, isodecyl, 6-methyldecyl and dodecyl esters.

Glyceryl ester groups are glycerol, esterified at either position 1 or 2 to the compound herein, and at the remaining two hydroxyl groups to, for example, stearic, oleic, myristic, oleic, or linoleic acid.

Salts derived from inorganic bases include sodium, potassium, lithium, ammonium, calcium, magnesium, ferrous, zinc, copper, manganous, aluminum, ferric, maganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic nontoxic bases are isopropylamine, diethylamine, ethanolamine, tromethamine, dicyclohexylamine, choline and caffeine.

"Lower alkyl" means a branched or unbranched saturated hydrocarbon chain containing 1 to 6 carbon atoms, e.g., methyl, n-butyl, i-hexyl and the like.

"Lower alkoxyl" means $-OR^1$ wherein in $R^1$ is lower alkyl as herein defined.

"Lower alkoxycarbonyl" refers to the substituent

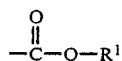

wherein $R^1$ is lower alkyl as previously defined.

"Lower alkylcarbonyl" refers to the substituent

wherein $R^1$ is lower alkyl as previously defined.

"Sulfonic acid" refers to the group $-SO_3H$;

"Sulfonic acid alkyl ester" refers to the group $-SO_3R^1$ wherein $R^1$ is lower alkyl as previously defined.

"Inorganic acid" refers to compounds which, when dissolved in water, release hydrogen ion and an inorganic anion, such as, for example, hydrochloric acid, sulfuric acid, phosphoric acid, and the like.

"Inorganic base" refers to compounds which, when dissolved in water, release hydroxide ion, either from their own substance or by withdrawing a hydrogen ion from water. Such bases include sodium hydroxide, sodium carbonate, potassium phosphate and the like.

General Preparation Parameters

Compounds of both formulas VI and VII contain a chiral center at the 1-position (that occupied by the carboxyl).

Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form, but is to encompass the individual optical isomers of the subject compounds.

If desired, racemic mixtures prepared herein may be resolved into their optical antipodes by conventional resolution means known per se, for example, by the separation (e.g., fractional crystallization) of the diastereomeric esters, amides, or salts formed by reaction of, e.g., racemic compounds of formula VI or VII with optically active alcohols, amines or bases.

Exemplary of such alcohols and amines are the optically active forms of 2-butanol, 2-pentanol, 3-methylcyclohexanol and the corresponding amines. Under different conditions, the above mentioned amines may be used to form the corresponding salts.

The separated pure diasteromeric salts, esters or amides may then be cleaved by standard means to afford the respective optical isomers of the compounds of formula VI or VII.

It is also to be understood that isolation of the compounds described herein, whether in the body of the specification or Examples, can be effected, if desired, by any suitable separation or purification procedure, such as, for example, filtration, extraction, crystallization, column chromatography, thin-layer chromatography or thick-layer chromatography, or a combination of these procedures. Specific illustrations of suitable separation and isolation procedures can be had by reference to the Examples hereinbelow. However, other equivalent separation or isolation procedures could, of course, also be used.

The salts of said compounds are also isolated by conventional means. For example, the reaction mixtures are evaporated to dryness, and the salts can be further purified by conventional methods.

The pharmaceutically acceptable non-toxic salt derivatives of the compounds of Formula VI and VII are prepared by treating the free acids with an appropriate amount of pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, maganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, isopropanol, butanol, acetone, dioxane or tetrahydrofuran. The molar ratio of compounds of Formula VI or VII to base used are chosen to provide the ratio desired for any particular salt. For preparing, for example, the calcium salts or magnesium salts the free acid starting material of Formula VI or VII can be treated with at least one-half molar equivalent of pharmaceutically acceptable base to yield a neutral salt. When the aluminum salts of the compounds of Formula VI or VII are prepared, at least one-third molar equivalent of the pharmaceutically acceptable base are employed if a neutral salt product is desired.

The salt derivatives of the compounds of Formula VI and VII can be reconverted to their respective free acids by acidifying said salts with an acid, preferably an inorganic acid, e.g., hydrochloric acid, sulfuric acid, and the like, at temperature of from about 0° C. to about 50° C., preferably at room temperature.

The pharmaceutically acceptable non-toxic esters of Formula VI and VII are prepared by esterifying the corresponding free acids with an alcohol reagent corresponding to the desired ester, e.g., an alkanol having up to 12 carbon atoms or with glycerol which is already esterified at two hydroxyls to other suitable acids. This reaction is conducted in the presence of a strong acid, such as boron trifluoride, hydrogen chloride, sulfuric acid, p-toluenesulfonic acid, and the like. If the alcohol reagent used in the esterification is a liquid at the reaction temperature, the alcohol reagent can be the reaction solvent. Optionally, the reaction can be carried out in an inert organic solvent in which the free acids and the alcohol reagent are soluble, such as a hydrocarbon solvent, e.g., hexane, isooctane, decane, cyclohexane, benzene, toluene, xylene, a halogenated hydrocarbon solvent, e.g., methylene chloride, chloroform, dichlorethane; or an ether solvent, e.g., diethyl ether, dibutyl ether dioxane, tetrahydrofuran, and the like. In the case where the alcohol reagent is a solid, the reaction preferably is conducted in a non-aqueous liquid inert organic solvent. The reaction is conducted at from about 0° C. to the reflux temperature of the reaction mixture, preferably using hydrogen chloride at a temperature of from 15° C. to about 35° C.

The product is isolated by conventional means such as diluting the reaction mixture with water, extracting the resulting aqueous mixture with a water-immiscible inert organic solvent, such as diethyl ether, benzene, methylene chloride, and the like, combining the extracts, washing the extracts with water to neutrality and then evaporating under reduced pressure.

The preferred acid esters are those ester derivatives prepared from methyl alcohol, ethyl alcohol, propyl alcohol, isopropyl alcohol, butyl alcohol, 2-butyl alcohol, isoamyl alcohol, pentyl alcohol, 2-pentyl alcohol, isopentyl alcohol, hexyl alcohol, 2-hexyl alcohol, isohexyl alcohol, heptyl alcohol, 2-heptyl alcohol, isoheptyl alcohol, octyl alcohol, 2-octyl alcohol, isooctyl alcohol, nonyl alcohol, 2-nonyl alcohol, isononyl alcohol, decyl alcohol, 2-decyl alcohol, isodecyl alcohol, undecyl alcohol, dodecyl alcohol, and the like.

Alternatively, the alkyl esters can be prepared by transesterification, according to methods known in the art. It is preferred in preparing the esters via transesterification to go from a lower ester to a higher ester, e.g., from the methyl ester, for example, to the isoamyl ester, for example. However, by using a substantial excess of a lower alcohol, a higher ester can be transesterified to a lower ester; thus, for example, by using a substantial excess of ethanol, the hexyl ester is converted by the transesterification to the ethyl ester.

Steps in the Preparation Process

The compounds of Formula VI and VII are prepared in accordance with the following Reaction Sequence I, wherein R, X, and Y are as previously defined in the Summary of the Invention, and $R^2$ is lower alkyl.

FIG. I

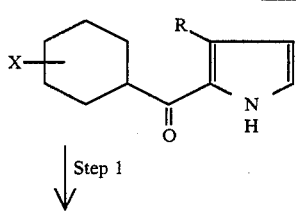

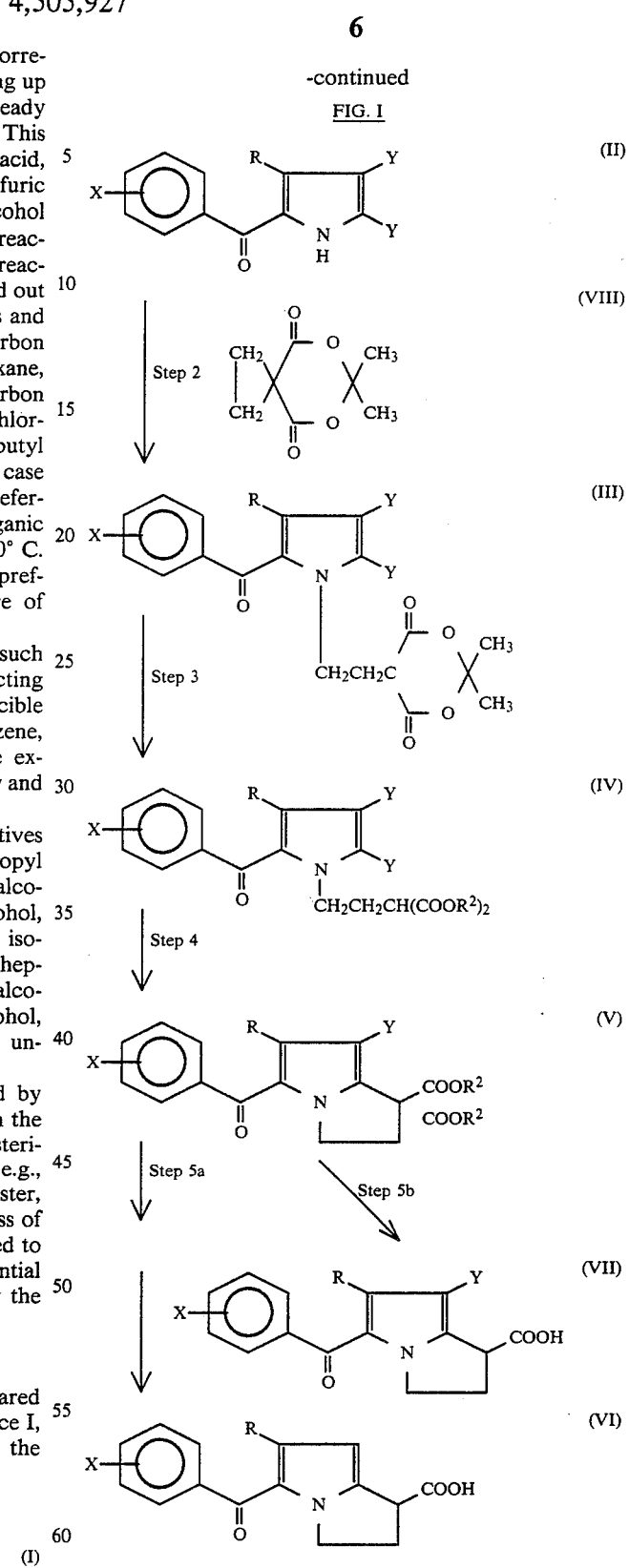

A. Preparation of the
5-benzoyl-7-halo-1,2-dihydro-3H-pyrrolo[1,2-a]pyrrole-1,1-dicarboxylates Compounds of the formula

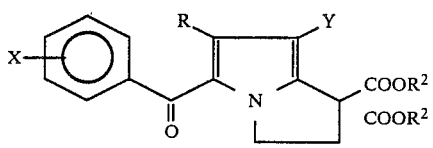

wherein:
R is hydrogen or lower alkyl;
X is hydrogen, lower alkyl, lower alkoxyl, lower alkoxycarbonyl, carboxyl, lower alkyl carbonyl, sulfonic acid, sulfonic acid alkyl ester, fluoro, chloro or bromo; and
Y is chloro or bromo,
and each $R^2$ is independently lower alkyl are prepared according to the above shown Reaction Sequence 1.

Compounds of the formulas II, III, IV and V as shown therein are novel, and are useful as intermediates in organic synthesis, in particular in the process described herein.

Benzoylpyrroles of formula I wherein R and X are as hereinbefore defined are prepared according to the method of White, *J Org Chem* 42: 4248 (1977), by reacting the appropriate pyrrole or 3-alkylpyrrole with the pertinent aroylamide.

Halogenation of compounds of formula I, accomplished in step 1 of the sequence shown, is carried out by treating the subject compound with a large excess of bromine or chlorine in the presence of an aprotic non-polar organic solvent. The halogen solution is added slowly to the substrate solution over a period of about 10 minutes to 5 hours, preferably 1–1.5 hours, at low temperature of about −10° to +10°, preferably 0°–2° until addition is complete. Constant stirring is preferred. The reaction is continued at higher temperature, about 10°–40°, preferably room temperature (15°–25°) for about 10 minutes to 10 hours, preferably 2 to 3 hours. The product, a compound of formula II, may be isolated by conventional means.

The conversion of compounds of formula II into the corresponding compounds of formula III (step 2) is effected by treatment with a slight excess of an alkali metal hydride, preferably sodium hydride in the presence of a polar aprotic organic solvent, e.g., DMF, glyme, diglyme, and the like, preferably dimethylformamide. The reaction is done under an inert atmosphere, such as neon, argon, nitrogen and the like, preferably argon. The reaction is slowed by cooling and kept at about 0°–50°, preferably 15°–25°, until it is clear the reaction is under control and then allowed to remain at approximately room temperature for about 15 minutes to 5 hours, preferably 1–2 hours. Subsequently, an excess of spiro[2.5]-5,7-dioxa-6,6-dimethyloctane-4,8-dione is added, and the temperature raised to about 50°–100°, preferably 65°–75°, and maintained for about 15 minutes to 5 hours, preferably 1.5–2.5 hours.

(Other corresponding spiro compounds of the general formula

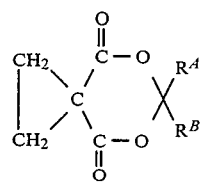

could also be used, wherein $R^A$ and $R^B$ are lower alkyl, but there is no particular advantage in doing so. The commonly prepared material is made from acetone and the diacid

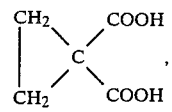

which diacid could also be reacted, for example, with methyl ethyl ketone (MEK) or with 3-pentanone to yield the 6-ethyl-6-methyl and the 6,6-diethyl analogs, respectively.)

After cooling, the product may be isolated if desired, or carried forward to the conversion into dialkyl ester represented herein in step 3.

Conversion to the dialkyl ester (step 3) is accomplished by treating a compound of formula III with an excess of lower alkyl alcohol, such as ethanol, propanol, i-butanol, and the like; but preferably with methanol in the presence of acid. Any mineral acid, e.g., sulfuric, phosphoric, etc., will serve, but hydrochloric acid is preferred. The reaction takes place at low temperature about (−10° to +10°) but preferably at 0°–2°, and is accomplished in about 15 minutes to 10 hours, usually 2–5 hours. The product, a compound of formula IV may then be isolated.

Cyclization of compounds of formula IV, step 4 herein, is effected by treating the subject compound with an excess strong base in inert solvent, preferably an alkali metal hydride in an aprotic polar organic solvent, most preferably sodium hydride in dimethylformamide. The reaction is done in an inert atmosphere, preferably under nitrogen. The reaction takes place in a temperature range of about 20°–100°, preferably 65°–75°, over a period of about 10 minutes to 10 hours, preferably 1–2 hours. The product may then be isolated and purified according to the usual techniques known to those skilled in the art. Said product, a compound of formula V, may then be converted as hereinafter described to compounds of formula VI or VII.

B. Decarboxylation of Dicarboxylate Precursors

Compounds of both formulas VI and VII are prepared by decarboxylating a compound of formula V wherein R, X and Y are as previously defined and $R^2$ is hydrogen or lower alkyl. If a compound of formula VI is desired, the halo atom at position 7 is removed by catalytic hydrogenation before, after, or during the decarboxylation process. In this case, as hereinbefore stated, X cannot be chloro or bromo in the compound of formula VI, because X will then be removed, as well as Y, during the hydrogenation. The precursors to VI, however, may, of course, have the choro or bromo substitution in the phenyl nucleus.

The decarboxylation procedure consists of treatment of a compound of formula V with base to generate the free carboxylate groups, followed by treatment with acid to liberate CO$_2$. In the special case wherein R$^2$ is hydrogen, the carboxylates are already free, and the treatment with base may be omitted. Even where R$^2$ is lower alkyl, it is possible to carry out the entire reaction by prolonged treatment with acid. However, deesterification is, in that case, much slower, and the preferred method is to treat sequentially with base and acid.

In the preferred embodiment of this invention, the base used is a dilute inorganic base, e.g., sodium hydroxide, sodium carbonate, potassium hydroxide and the like in an aqueous or polar organic solvent or mixture thereof, under inert atmospheric conditions (i.e., argon, nitrogen); and the acid is a dilute inorganic acid, e.g., nitric acid, sulfuric acid hydrochloric acid and the like.

The divergence of the decarboxylation steps from the common formula V intermediate is shown as steps 5a and 5b of Reaction Sequence I.

Step 5a, the conversion to the deshalo compound, the dicarboxylate of formula V involves three processes: deesterification by treatment with base, decarboxylation by treatment with acid, and dehalogenation by hydrogenating in the presence of a catalyst. While deesterification must, of course, precede decarboxylation (though as hereinbefore stated, deesterification may be, though poorly, accomplished by treatment with acid); the dehalogenation may be carried out at any point in the sequence—before treatment with base, before treatment with acid, but after treatment with base, or after both base and acid treatments. Intermediates in the sequence may, but need not be, and preferably are not, isolated. There is some small advantage to the sequence base—hydrogen—acid in that the dianion formed by treatment with base is more water soluble than the diester or diacid and permits polar solvents in the hydrogenation process to be used more effectively, but the other sequences are also practicable.

In the deesterification, V is treated with an excess of inorganic base, e.g., potassium carbonate, sodium carbonate, calcium hydroxide, potassium hydroxide and the like, preferably sodium hydroxide in a polar aqueous solvent, e.g., methanol-water, ethanol-water, acetone-water; preferably methanol water. The reaction mixture is heated to about 30° to 100°, preferably 80°-90° under an inert atmosphere, preferably argon. The reaction is allowed to proceed for about 10 minutes to 10 hours, preferably 1-2 hours. The product salt may, if desired, be purified, or recovered in crude form.

Hydrogenation is carried out by treatment of the ester, salt, decarboxylated monoacid (or other intermediate resulting from acid or base treatment with hydrogen gas in the presence of a suitable hydrogenation catalyst such as platinum on charcoal, finely divided nickel, and the like, a base to absorb the liberated HY, such as NaOH, Na$_2$CO$_3$ or MgO; and solvent, e.g., ethanol, methanol, water and the like. A preferred hydrogenation catalyst is 5% palladium-on-charcoal, and a preferred base is MgO. A preferred solvent is aqueous methanol. The reaction mixture is hydrogenated at about 10°-50°, preferably room temperature (15°-25°) and at about 1-4 atm, preferably atmospheric pressure for about 10 minutes to 10 hours, preferably 1-3 hours.

In the decarboxylation step, the deesterified dicarboxylate, with or without the halogen is treated with acid. Any strong inorganic acid, e.g., hydrochloric, sulfuric, phosphoric and the like may be used, but hydrochloric is preferred. Concentrations of about 0.2N to 6N, preferably 0.5N-1.5N are used, and reaction is continued for about 10 sec. to a hour, preferably several minutes in any aqueous solvent, preferably just water. The product, a compound of formula VI or VII may then be isolated by conventional means.

Step 5b, in which the 7-halo substitutent is retained, is carried out in a manner identical to that described above for step 5a, as to treatment with base and acid; the hydrogenation process is simply omitted.

Representative Syntheses

Representative starting materials, intermediates and products to which the sequence of reactions shown in Reaction Sequence I is applicable are shown below. The compounds therein are illustrative and not all-inclusive of the invention.

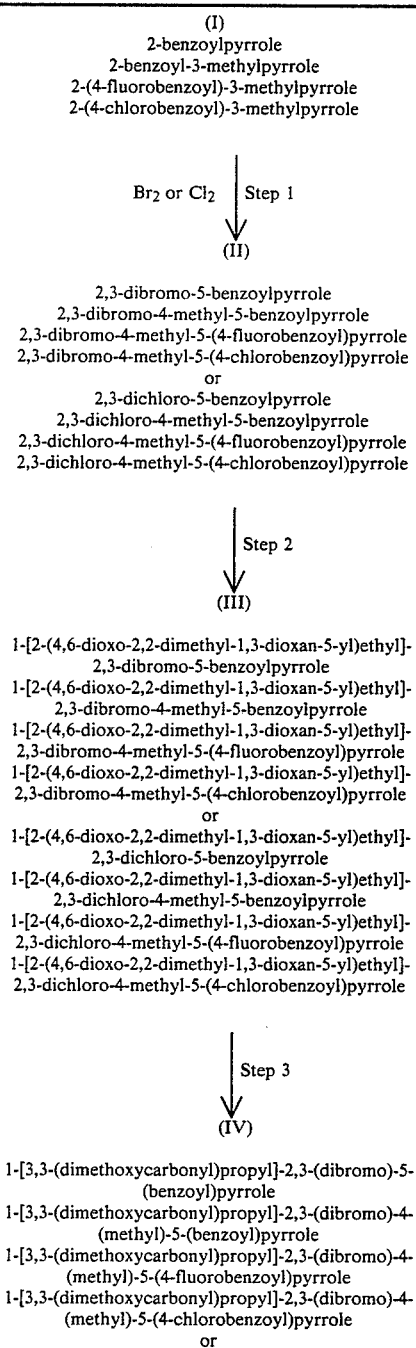

(I)
2-benzoylpyrrole
2-benzoyl-3-methylpyrrole
2-(4-fluorobenzoyl)-3-methylpyrrole
2-(4-chlorobenzoyl)-3-methylpyrrole Br$_2$ or Cl$_2$ | Step 1

(II)

2,3-dibromo-5-benzoylpyrrole
2,3-dibromo-4-methyl-5-benzoylpyrrole
2,3-dibromo-4-methyl-5-(4-fluorobenzoyl)pyrrole
2,3-dibromo-4-methyl-5-(4-chlorobenzoyl)pyrrole
or
2,3-dichloro-5-benzoylpyrrole
2,3-dichloro-4-methyl-5-benzoylpyrrole
2,3-dichloro-4-methyl-5-(4-fluorobenzoyl)pyrrole
2,3-dichloro-4-methyl-5-(4-chlorobenzoyl)pyrrole Step 2

(III)

1-[2-(4,6-dioxo-2,2-dimethyl-1,3-dioxan-5-yl)ethyl]-2,3-dibromo-5-benzoylpyrrole
1-[2-(4,6-dioxo-2,2-dimethyl-1,3-dioxan-5-yl)ethyl]-2,3-dibromo-4-methyl-5-benzoylpyrrole
1-[2-(4,6-dioxo-2,2-dimethyl-1,3-dioxan-5-yl)ethyl]-2,3-dibromo-4-methyl-5-(4-fluorobenzoyl)pyrrole
1-[2-(4,6-dioxo-2,2-dimethyl-1,3-dioxan-5-yl)ethyl]-2,3-dibromo-4-methyl-5-(4-chlorobenzoyl)pyrrole
or
1-[2-(4,6-dioxo-2,2-dimethyl-1,3-dioxan-5-yl)ethyl]-2,3-dichloro-5-benzoylpyrrole
1-[2-(4,6-dioxo-2,2-dimethyl-1,3-dioxan-5-yl)ethyl]-2,3-dichloro-4-methyl-5-benzoylpyrrole
1-[2-(4,6-dioxo-2,2-dimethyl-1,3-dioxan-5-yl)ethyl]-2,3-dichloro-4-methyl-5-(4-fluorobenzoyl)pyrrole
1-[2-(4,6-dioxo-2,2-dimethyl-1,3-dioxan-5-yl)ethyl]-2,3-dichloro-4-methyl-5-(4-chlorobenzoyl)pyrrole Step 3

(IV)

1-[3,3-(dimethoxycarbonyl)propyl]-2,3-(dibromo)-5-(benzoyl)pyrrole
1-[3,3-(dimethoxycarbonyl)propyl]-2,3-(dibromo)-4-(methyl)-5-(benzoyl)pyrrole
1-[3,3-(dimethoxycarbonyl)propyl]-2,3-(dibromo)-4-(methyl)-5-(4-fluorobenzoyl)pyrrole
1-[3,3-(dimethoxycarbonyl)propyl]-2,3-(dibromo)-4-(methyl)-5-(4-chlorobenzoyl)pyrrole
or 1-[3,3-(dimethoxycarbonyl)propyl]-2,3-(dichloro)-5-
(benzoyl)pyrrole
1-[3,3-(dimethoxycarbonyl)propyl]-2,3-(dichloro)-4-
(methyl)-5-(benzoyl)pyrrole
1-[3,3-(dimethoxycarbonyl)propyl]-2,3-(dichloro)-4-
(methyl)-5-(4-fluorobenzoyl)pyrrole
1-[3,3-(dimethoxycarbonyl)propyl]-2,3-(dichloro)-4-
(methyl)-5-(4-chlorobenzoyl)pyrrole Step 4 ↓

(V)

dimethyl [5-benzoyl-7-bromo-1,2-dihydro-3H—pyrrolo-
[1,2-a]pyrrole]-1,1-dicarboxylate
dimethyl [5-benzoyl-6-methyl-7-bromo-1,2-dihydro-3H—
pyrrolo[1,2-a]pyrrole]-1,1-dicarboxylate
dimethyl [5-(4-fluorobenzoyl)-6-methyl-7-bromo-1,2-
dihydro-3H—pyrrolo[1,2-a]pyrrole]-1,1-dicarboxylate
dimethyl [5-(4-chlorobenzoyl)-6-methyl-7-bromo-1,2-
dihydro-3H—pyrrolo[1,2-a]pyrrole]-1,1-dicarboxylate
or
dimethyl [5-benzoyl-7-chloro-1,2-dihydro-3H—
pyrrolo[1,2-a]pyrrole]-1,1-dicarboxylate
dimethyl [5-benzoyl-6-methyl-7-chloro-1,2-dihydro-3H—
pyrrolo[1,2-a]pyrrole]-1,1-dicarboxylate
dimethyl [5-(4-fluorobenzoyl)-6-methyl-7-chloro-
1,2-dihydro-3H—pyrrolo[1,2-a]pyrrole]-1,1-dicarboxylate
dimethyl [5-(4-chlorobenzoyl)-6-methyl-7-chloro-
1,2-dihydro-3H—pyrrolo[1,2-a]pyrrole]-1,1-dicarboxylate, Step 5a ↙     Step 5b ↘

(VI)                              (VII)

5-benzoyl-1,2-dihydro-3H—         5-benzoyl-7-bromo-1,2-dihydro-
pyrrolo[1,2-a]pyrrole-1-          3H—pyrrolo[1,2-a]pyrrole-
carboxylic acid,                  1-carboxylic acid,
4-methyl-5-benzoyl-1,2-           4-methyl-5-benzoyl-7-bromo-1,2-
dihydro-3H—pyrrolo[1,2-           dihydro-3H—pyrrolo[1,2-a]-
a]pyrrole-1-carboxylic            pyrrole-1-carboxylic acid,
acid,                             4-methyl-5-(4-fluorobenzoyl)-
4-methyl-5-(4-fluoro-             7-bromo-1,2-dihydro-3H—
benzoyl)-1,2-dihydro-3H—          pyrrolo[1,2-a]-pyrrole-1-
pyrrolo[1,2-a]-pyrrole-1-         carboxylic acid,
carboxylic acid,                  4-methyl-5-(4-chlorobenzoyl)-
and                               7-bromo-1,2-dihydro-3H—
5-benzoyl-1,2-dihydro-3H—         pyrrolo[1,2-a]-pyrrole-1-
pyrrolo[1,2-a]pyrrole-1-          carboxylic acid
carboxylic acid,                  or
(as would have been               5-benzoyl-7-chloro-1,2-
obtained with an                  dihydro-3H—pyrrolo[1,2-a]-
originally unsubstituted          pyrrole-1-carboxylic acid,
phenyl).                          4-methyl-5-benzoyl-7-chloro-
                                  1,2-dihydro-3H—pyrrolo[1,2-a]-
                                  pyrrole-1-carboxylic acid,
                                  4-methyl-5-(4-fluorobenzoyl)-
                                  7-chloro-1,2-dihydro-3H—
                                  pyrrolo[1,2-a]-pyrrole-1-
                                  carboxylic acid,
                                  4-methyl-5-(4-chlorobenzoyl)-
                                  7-chloro-1,2-dihydro-3H—
                                  pyrrolo[1,2-a]-pyrrole-1-
                                  carboxylic acid.

Alternative Process for Synthesis of Compounds of
formula VII, and production of the 6,7-dihalo
compounds as by-products thereof In addition to preparation of the 7-halo compounds of formula VII, by the process of the present invention, said compounds, along with the corresponding 6,7-dihalo compounds, may be prepared by direct halogenation of the compounds of formula VI, which have first been esterified. Procedures for esterification have been described previously herein.

In the direct bromination, the lower alkyl ester of a compound of formula VI is dissolved in a polar solvent, such as acetic acid. Bromine, preferably dissolved in the same solvent, is then added with stirring until reaction is complete. If the 6,7 dihalo compound is desired, a 2:1 ratio of bromine to substrate compounds is used; if the 7-bromo compound is desired, a 1:1 ratio is used. The reaction mixture is worked up using standard procedures to isolate the halogenated product. The halogenated product may then be hydrolyzed to form the free acid by procedures known in the art, such as, for example, treatment with aqueous or alcoholic base.

In the direct chlorination, the lower alkyl ester of a compound of formula VI is dissolved in an appropriate non-polar solvent; such as chloroform, in the presence of a basic salt, such as calcium carbonate, and treated with a solution of chlorine, preferably in the same solvent. When an equimolar mixture of chlorine and substrate is used, both the 6,7 dihalo and the 7-halo derivatives are formed. Both can be isolated by conventional means. Both can then be converted to the free acids by the usual techniques know in the art.

Specific examples of these alternative processes are given hereinbelow. Of course, in the above procedures, the compounds of formula VI in which R is lower alkyl yield only the 7-halo, not 6,7-dihalo derivatives.

PREFERRED EMBODIMENTS

Preferred embodiments of compounds of formula VII, useful for their antinflammatory, antipyretic and analgesic properties, their properties as aggregation inhibitors and fibrinolytic agents, and as smooth muscle relaxants, are those wherein R is hydrogen or methyl.

Another preferred set of embodiments is that wherein X is hydrogen, methyl, fluoro, chloro or bromo.

Another preferred embodiment is that wherein Y is chloro.

A more preferred set of embodiments is that wherein R is hydrogen or methyl and X is hydrogen, methyl, fluoro, chloro or bromo; and a still more preferred embodiment is that wherein R is hydrogen or methyl, X is hydrogen, methyl, fluoro, chloro or bromo and Y is chloro.

Preferred embodiments of the process for preparing compounds of formula VII are those wherein R, X, and Y are defined so as to generate the compounds described as preferred hereinabove.

Preferred embodiments of the process for preparing the compounds of formula VI are those wherein R is hydrogen or methyl or X is hydrogen, methyl, or fluoro, or most preferably both.

UTILITY AND ADMINISTRATION

The compounds of Formula VII and the pharmaceutically acceptable non-toxic esters and salts thereof, are useful as anti-inflammatory agents, analgesic agents, platelet aggregation inhibitors, fibrinolytic agents, and as smooth muscle relaxants. These compounds can be used both prophylactically and therapeutically.

Those compounds of formula VI described herein which are novel; i.e. those compounds of formula VI wherein X is lower alkoxylcarbonyl, carboxyl, lower alkylcarbonyl, sulfonic acid, or sulfinic acid alkyl ester, and the pharmaceutically acceptable non-toxic esters and salts thereof, are likewise useful, in the same fashion and at the same general level of activity.

The compositions containing these compounds are thus useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Initial small animal screening tests to determine anti-inflammatory activity potential include the carrageenin induced paw inflammation in the rat according to the method of Winter, et al. (*Proc. Soc. Exp. Biol. Med.* 111:544–547, 1962) and the cotton pellet granuloma test in the rat according to the method of Meier, et al. (*Experientia* 6:469–471, 1950) and modifications thereof.

In addition, in certain cases, the anti-inflammatory activity may be evaluated by using the adjuvant arthritis assay according to the method of Pearson (*Proc. Soc. Exp. Biol. Med.* 91:95–101, 1956). Also, in vitro tests, for example those using synovial explants from patients with rheumatoid arthritis, Dayer et al. (*J. Exp. Med.* 145:1399–1404, 1977), are useful in determining whether compounds exhibit anti-inflammatory activity.

Small animal screening tests to determine analgesic activity potential include the mouse analgesic (anti-writhing) assay according to the method of Hendershot and Forsaith, (*J. Pharmacal. Exp. Thev.* 125:237–240, 1959).

Generally, the antipyretic activity potential is indicated by the anti-inflammatory potential as measured by the previously mentioned assays.

Platelet aggregation inhibition potential and fibrinolytic activity is determined by using turbidimetric method of Born (*J. Physiol.* (*Lond*) 162:67–68p, 1962).

Potential activity as a smooth muscle relaxant is determined in vitro using the method of Vickery (*Prostaglandins Med* 2:299–315, 1979) or Vickery (*Prostaglandins Med* 2:225–235, 1979).

Administration of the active compounds of Formula VI or VII and the pharmaceutically acceptable, non-toxic esters and salts thereof, in an appropriate pharmaceutical composition can be via any of the accepted modes of administration of agents for the treatment of inflammation, pain or pyrexia, or the prophylaxis thereof. Thus, administration can be for example, orally, parenterally or topically, in the form of solid, semi-solid or liquid dosage forms, such as, for example, tablets, suppositories, pills, capsules, powders, solutions, suspensions, emulsions, creams, lotions, ointments or the like, preferably in unit dosage forms suitable for simple administration of precise dosages. The compositions will include a conventional pharmaceutical carrier or excipient and an active compound of Formula VI or VII and the pharmaceutically acceptable non-toxic esters and salts thereof, and, in addition, may include other medicinal agents, pharmaceutical agents, carriers, adjuvants, etc.

Generally the composition will contain 0.1% to 95% by weight of the active compound and the balance excipients. The preferable range depends, of course, on the mode of administration—oral dosages in the form of tablets, for example 25–95%; topical or intravenous formulations 0.1–5%.

The preferred manner of administration, for the conditions detailed above, is oral using a convenient daily dosage regimen which can be adjusted according to the degree of affliction. Generally, a daily dose of from 25 to 500 mg. of the active compound of Formula VI or VII and the pharmaceutically acceptable, non-toxic esters and salts thereof is used. Most conditions respond to treatment comprising a dosage level of the order of 0.5 to 6 mg. per kilogram of body weight per day. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccarine, talcum, cellulose, glucose, gelatin, sucrose, magnesium carbonate, and the like. Such compositions take the form of solutions, suspensions, tablets, pills, capsules, powders, sustained release formulations and the like.

The active compounds of Formula VI or VII and the pharmaceutically acceptable, non-toxic esters and salts thereof, may be formulated into a suppository using, for example, polyalkylene glycols, for example, polypropylene glycol, as the carrier. Liquid pharmaceutically administerable composition can, for example, be prepared by dissolving, dispersing, etc. an active compound, as described above, and optional pharmaceutical adjuvants in a carrier, such as, for example, water, saline, aqueous dextrose, glycerol, ethanol and the like, to thereby form a solution or suspension. If desired, the pharmaceutical composition to be administered may also contain minor amount of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's *Pharmaceutical Sciences*, Mack Publishing Company, Easton, Pa., 14th. Edition, 1970. The composition to be administered will, in any event, contain a quantity of the active compound(s) in a pharmaceutically effective amount for relief of the particular condition being treated in accordance with the teachings of this invention.

The compounds of Formula VI or VII and the non-toxic, pharmaceutically acceptable esters and salts thereof, described above, are also platelet aggregation inhibitors and fibrinolytic agents. These compounds may be formulated into pharmaceutical compositions and administered in such manner as described above for their use as analgesics to subjects who are at risk by virtue of a tendency to form blood clots in the circulatory system. The dosage range and nature of the pharmaceutical compositions are as above described.

The compounds of Formula VI or VII and the non-toxic, pharmaceutically acceptable esters and salts thereof, described above, are also uterine smooth muscle relaxants and thus are useful as agents for maintaining the pregnancy of pregnant mammals, for the benefit of the mother and/or fetus, until termination of the pregnancy is considered, from a medical point of view, to be favorable, or more favorable, for the mother and/or the fetus. As stated hereinabove it should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

In particular, the compounds of Formula VI or VII and the pharmaceutically acceptable, non-toxic esters and salts thereof, are used as agents for delaying the onset of, or for postponing, parturition. As used in this application, the phrase "to delay the onset of parturition" is intended to cover that delay in parturition caused by the administration of compounds of and the pharmaceutically acceptable, non-toxic esters and salts thereof, at any time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experience later in the pregnancy when the fetus is considered to be "viable". In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time and is considered favorable to the mother and/or fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase "postponing parturition" is intended to cover that delay in parturition caused by the administration of the compounds of Formula VII and the pharmaceutically acceptable, non-toxic esters and salts thereof after uterine muscle contractions have begun. The condition of the patient, including the time within the gestation period when the contractions have begun, the severity of the contractions and how long the contractions have taken place will affect the results achieved with the administration of the compounds hereof. For Example, the effect can be to reduce the intensity and/or the duration of the contractions (the actual act of parturition being "prolonged"), or to stop the contractions altogether. In either case, the effect will be to prolong the gestation period although, depending upon the conditions of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formula VI or VII and the pharmaceutically acceptable, non-toxic esters and salts thereof, for the purposes set forth herein should be consistent with best and/or accepted medical (or veterinary) practices so as to maximize the benfits to the mother and the fetus. For example, administration should not be continued so long past full term that the fetus dies in utero.

In the practice of the methods of the present invention, a therapeutically effective amount of a compounds of Formula VI or VII and the pharmaceutically acceptable, non-toxic esters and salts thereof, or a pharmaceutical composition containing same, is administered to the pregnant mammal via any of the usual and acceptable methods known in the art. The compound can be adminstered either singly or in combination with another compound or compounds, as defined above, or other pharmaceutical agents, carriers, adjuvants, etc. Such compound(s) or compositions can be administered orally, parenterally, either in the form of solid, semisolid, or liquid dosage forms. Typically, administration is by a pharmaceutical composition containing the pharmaceutically active compound and one or more pharmaceutical carriers or adjuvants.

The administerable pharmaceutical composition may take the form of oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, gelatin sucrose, magnesium carbonate, and the like. The active compound as defined above may be formulated as suppositories using, for example, polyalkylene glycols, for example, polypropylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this area; for example, see Remington's *Pharmaceutical Sciences*, Mack Publishing Company, Easton, Pa., 14th Edition, 1970. The composition or formulation to be administered will, in any event, contain a quantity of the active compound(s) in an amount effective to delay the onset of parturition or to postpone parturition if uterine contractions have already begun. Generally a daily dose of from 0.5 to about 25 mg. of the active compound per kilogram of body weight will be administered, with administration being a single daily dose or up to three or four smaller dosages regularly given throughout the day. The amount of active compound administered will, of course, depend on its relative activity.

The following Examples illustrate the invention but are not intended to limit its scope. The abreviation TLC refers to thin-layer chromatography and all mixture ratios used with regard to liquids refer to volume ratios. Also where necessary, examples are repeated to prepare additional material for subsequent examples; and unless otherwise specified the reactions are carried out at room temperature (15° to 25° C.). The parethetical referencs to step numbers refer to Reaction Sequence 1.

EXAMPLE 1

A. Preparation of 2,3-dibromo-5-benzoylpyrrole (Step 1)

Bromine (15.16 g, 94.7 mmoles) in dichloromethane (250 ml) was added dropwise at 0°0 over a one hour and 10 minute period, with constant stirring, to a solution of 2-benzoylpyrrole [8.12 g, 4.75 mmoles; prepared according to White, J. Org. Chem. 42 4248, (1977)] in anhydrous dichloromethane (250 ml). The reaction was allowed to rise to room temperature and stirring was continued for 2.5 h. The solvent was evaporated to dryness and the crystalline residue was recrystallized from dichloromethane hexane. A total of 3 crops of the product (11.95 g, 76.5%) was obtained. Further product remained in the mother liquors. This substance had the following physical constants:

mp: 177°–177.5° corr. (hexane-dichloromethane).
UV: 206, 249, 314 nm ($\epsilon$10,500, 8700, 16,200).
IR: (CHCl$_3$) 3415, 1626, 1576 cm$^{-1}$.
NMR: (CDCl$_3$) 6.68 (s, 1H), 7.46–7.55 (m, 3H), 7.80–7.96 (m, 2H), 10.78 (s, 1H).
MS: 331, 329, 327 (M+).
Calcd. for C$_{11}$H$_7$Br$_2$NO: C, 40.15; H, 2.14; N, 4.26; Br, 48.58. Found: C, 40.10; H, 2.11; N, 4.19; Br, 48.62.

B. In a similar manner, compounds of formula I in which the benzoyl moiety is substituted and/or a 3-alkyl substituent is present on the pyrrole are halogenated to give the corresponding 2,3-dibromo analogs of 2,3-dibromo-5-benzoylpyrrole. For example,
2-benzoyl-3-n-butylpyrrole;
2-(4-methylbenzoyl)-3-methylpyrrole;
2-(3-ethoxycarbonylbenzoyl)-3-ethylpyrrole; and
2-(2-methoxysulfonylbenzoyl)pyrrole
may be treated in accordance with the procedure in A to give, respectively,
2,3-dibromo-4-n-butyl-5-benzoylpyrrole;
2,3-dibromo-4-methyl-5-(4-methylbenzoyl)pyrrole;
2,3-dibromo-4-ethyl-5-(3-ethoxycarbonylbenzoyl)pyrrole; and
2,3-dibromo-5-(2-methoxysulfonylbenzoyl)pyrrole.

C. In a similar manner substituting the corresponding numbers of moles of chlorine for bromine in the procedure of part A, and using 2-benzoylpyrrole or the 2-aroyl pyrroles listed in part B of the example, one obtains
2,3-dichloro-5-benzoylpyrrole;
2,3-dichloro-4-n-butyl-5-benzoylpyrrole;
2,3-dichloro-4-methyl-5-(4-methylbenzoyl)pyrrole;
2,3-dichloro-4-ethyl-5-(3-ethoxycarbonylbenzoyl)pyrrole; and
2,3-dichloro-5-(2-methoxysulfonylbenzoyl)pyrrole.

EXAMPLE 2

A. A preparation of dimethyl[2-(2,3-dibromo-5-benzoylpyrrol-1-yl)ethyl]-malonate (Steps 2 and 3)

50% Sodium hydride in mineral oil (1.06 g, 22.1 mmoles) was added in two portions with stirring to a solution of 2,3-dibromo-5-benzoylpyrrole (6.52 g, 19.8 mmoles) in anhydrous dimethylformamide, (50 ml) which was maintained in an atmosphere of argon. During the addition of the sodium hydride moderation of the temperature was provided by means of an ice bath. When the initial vigorous reaction was over, the mixture was stirred at room temperature for 50 min. To this solution was added spiro [2.5]-5,7-dioxa-6,6-dimethyloctane-4,8-dione (3.50 g, 20.6 mmoles) prepared according to S. Danishefsky, J. Org. Chem. 40, 2969 (1975). The temperature of the mixture was slowly raised. When a bath temperature of 70° was reached (20 min.), a colorless precipitate began to form. The temperature of the heating bath was maintained at 75°–80° for 2 hours. At this time an additional quantity (0.350 g) of the spiro compound was added. After 4 hours at 75°–80°, the reaction mixture was cooled to room temperature. Anhydrous diethyl ether (500 ) was added with stirring and the precipitated solid was collected by filtration on a porous glass disk. The precipitated material sodium salt of 1-[2-(4,6dioxo-2,2-dimethyl-1,3-dioxan-5-yl)-ethyl]-2,3-(dibromo)-5-(benzoyl)pyrrole was washed well with dry ether and then dried in vacuo to give the solid salt 9.92 g. of (93.5%) a non-hydroscopic cream colored powder identified as sodium salt of 1-[2-(4,6-dioxo-2,2-dimethyl-1,3-dioxan-5-yl)ethyl]-2,3-(dibromo)-5-(benzoyl)-pyrrole.

A saturated solution of hydrogen chloride in methanol (200 ml) was prepared at 0°. To the solution at 0° was added the above sodium salt. The suspension was stirred at this temperature for 2 hours diluted with additional methanol (200 ml) and slowly allowed to rise to room temperature. After a total elapsed time of 5 hours, the methanol was evaporated at 10°–20° in vacuo. The resulting semi-solid was partitioned between ether (600 ml) and water (300 ml). The phases were separated and the water layer was extracted with additional ether (200 ml). The organic layers were combined, washed with water, dried over sodium sulfate and evaporated to dryness to give a nearly colorless oil (8.44 g). This material was dissolved in the minimum amount of ether and filtered through a column of flurosil (100 g) to remove a small amount of a colored impurity. Elution with ether gave, after evaporation of the solvent, a colorless oil (8.26 g, 86%) which was homogeneous by thin layer chromatography. The oil on seeding crystallized and after trituration with hexane a colorless crystalline mass was formed. This material was recrystallized from ether-hexane to give dimethyl[2-(2,3-dibromo-5-benzoylpyrrol-1-yl)ethyl]malonate having the following characteristics:

mp: 96–96.5° corr. (ether-hexane).
UV: 256, 315 nm ($\epsilon$9550, 14,800).
IR: (CHCl$_3$) 1756, 1740, 1636, 1603, 1582 cm$^{-1}$.
NMR: (CDCl$_3$) 2.39 (q, 2H, J=7.3), 3.50 (t, 1H, J=7.3), 3.73 (s, 6H), 4.54 (t, 2H, J=7.3), 6.75 (s, 1H), (7.34–7.84 (m, 5H).
MS: 489, 487, 485 (M+).

B. In a similar manner, the 2,3-dibromo compounds illustrated in part B of Example 1 are submitted to the procedure in A, above, and converted to, respectively
dimethyl [2-(2,3-dibromo-4-n-butyl-5-benzoylpyrrol-1-yl)-ethyl]malonate;
dimethyl [2-(2,3-debromo-4-methyl-5-(4-methyl-benzoyl)-pyrrol-1-yl)ethyl]malonate;
dimethyl [2-(2,3-dibromo-4-ethyl-5-(3-ethoxy-carbonylbenzoyl-pyrrole-1-yl)ethyl]malonate;
dimethyl [2-(2,3-dibromo-5-(2-methoxysulfonyl-benzoyl)-pyrrol-1-yl)ethyl]malonate.

C. Similarly, substituting for 2,3-dibromo-5-benzoylpyrrole the compounds listed in Example 1 part C into the procedure of Part A herein, one obtains
dimethyl [2-(2,3-dichloro-5-benzoylpyrrol-1-yl)-ethyl]-malonate;
dimethyl [2-(2,3-dichloro-4-n-butyl-5-benzoylpyrrol-1-yl)-ethyl]malonate;
dimethyl [2-(2,3-dichloro-4-methyl-5-(4-methyl-benzoyl)-pyrrol-1-yl)ethyl]malonate;
dimethyl [2-(2,3-dichloro-4-ethyl-5-(3-ethoxy-carbonylbenzoyl-pyrrole-1-yl)ethyl]malonate;
dimethyl [2-(2,3-dichloro-5-(2-methoxysulfonylbenzoyl)-pyrrol-1-yl)ethyl]malonate.

EXAMPLE 3

A. Preparation of dimethyl 5-benzoyl-7-bromo-1,2-dihydro-3H-pyrrolo[1,2-a]pyrrole-1,1-dicarboxylate (Step 4)

50% sodium hydride in mineral oil (0.030 g, 0.6 mmoles) was added in one portion with stirring to a solution of the above acyclic diester (0.244 g, 0.5 mmoles) in anhydrous dimethylformamide (2 ml) maintained in a nitrogen atmosphere. In 20 min. a homogeneous yellow orange solution was obtained. The reaction mixture was then slowly heated in an oil bath and gradually turned dark red. After a bath temperature of 75° was attained (30 min.), the color began to fade. After stirring for 1 hour, 45 minutes, the mixture was cooled and poured into ether. Extraction with water removed some yellow colored side products, the ether phase was washed with water, dried over sodium sulfate and evaporated to dryness to afford an oil (0.235 g). This material was filtered through a short column of florosil using ether as the solvent. Thin layer chromatography of the material thus obtained showed the presence of a trace of the starting material followed by a minor product overlapping with a single major product. The material was purified high pressure liquid chromatograph using a (50 cm × 9.5 mm) Lichrosorb column. The developing solvent was ethyl acetate hexane (15–85) at flow rate of 8 ml/min. and a pressure of 1200 psi. A minor product (0.025 g) had a 17.5 min. retention time. The major product, having a retention time of 20 min. (0.164 g., 81% yield), was isolated as a colorless oil which crystallized upon trituration with ethyl-acetate. Upon recrystallization from hexane, dimethyl 5-benzoyl-7-bromo-1,2-dihydro-3H-pyrrolo[1,2-a]-pyrrole-1,1-dicarboxylate was obtained which exhibited the following characteristics:

mp: 109–109.5° corr. (hexane).

UV: 211, 254, 314 nm ($\epsilon$10,700, 8120, 15,500).

IR: (CHCl$_3$) 1743, 1631, 1604, 1581 cm$^{-1}$.

NMR: (CDCl$_3$) 3.16 (t, 2H, J=6.6), 3.82 (s, 6H), 4.52 (t, 2H, J=6.6), 6.82 (s, 1H), 7.44–7.52 (m, 3H), 7.68–7.87 (m, 2H),

MS: 407, 405 (M+).

Calcd. for C$_{18}$H$_{16}$Br NO$_5$: C, 53.22; H, 397; BR, 19.69: N, 3.45. Found: C, 53.32; H, 3.93; Br, 19.43; N, 3.41.

The minor product had NMR spectral characteristics which were consistant with that expected for methyl[5-benzoyl-7-bromo-1,2-dihydro-3H-pyrrolo[1,2-a]pyrrole-1-] carboxylate:

NMR: (CDCl$_3$) 2.75–3.04 (m, 2H), 3.73 (s, 3H), 3.87–4.08 (m, 1H), 4.42–4.65 (m, 2H), 6.74 (s, 1H), 7.41–7.55 (m, 3H), 7.68–8.00 (m, 2H).

B. Similarly, applying the procedures of A, above, the compounds listed in part B of Example 2 are converted to, respectively dimethyl [6-n-butyl-5-benzoyl-7-bromo-1,2-dihydro-3H-pyrrolo[1,2-a]pyrrole]1,1-dicarboxylate;

dimethyl [5-(4-methylbenzoyl)-6-methyl-7-bromo-1,2-dihydro-3H-pyrrolo[1,2-a]pyrrole]-1,1-dicarboxylate;

dimethyl [5-(3-ethoxycarbonylbenzoyl)-6-ethyl-7-bromo-1,2-dihydro-3H-pyrrolo[1,2-a]pyrrole]-1,1-dicarboxylate; and dimethyl 5-(2-methoxysulfonylbenzoyl)-7-bromo-1,2-dihydro-3H-pyrrolo[1,2-a]pyrrole]-1,1-dicarboxylate.

C. Similarly, applying the procedure of Part A of this example to the compounds listed in Example 2, part C, one obtains:

dimethyl [5-benzoyl-7-chloro-1,2-dihydro-3H-pyrrolo-[1,2-a]pyrrole]1,1-dicarboxylate;

dimethyl [6-n-butyl-5-benzoyl-7-chloro-1,2-dihydro-3H-pyrrolo[1,2-a]pyrrole]1,1-dicarboxylate;

dimethyl [5-(4-methylbenzoyl)-6-methyl-7-chloro-1,2-dihydro-3H-pyrrolo[1,2-a]pyrrole]-1,1-dicarboxylate;

dimethyl [5-(3-ethoxycarbonylbenzoyl)-6-ethyl-7-chloro-1,2-dihydro-3H-pyrrolo[1,2-a]pyrrole]-1,1-dicarboxylate; and dimethyl [5-(2-methoxysulfonylbenzoyl)-7-chloro-1,2-dihydro-3H-pyrrolo[1,2-a]pyrrole]-1,1-dicarboxylate.

EXAMPLE 4

A. Preparation of 5-benzoyl-1,2-dihydro-3H-pyrrolo-[1,2-a]pyrrole-1-carboxylic acid (Step 5a)

Dimethyl 5-benzoyl-7-bromo-1,2-dihydro-3H-pyrrolo-[1,2-a]pyrrole-1,1-dicarboxylate (2.04 g 5.0 mmoles) was dissolved in methanol (100 ml) and water (10 ml), and sodium hydroxide (0.40 g, 10 mmoles) was added. This solution was heated at reflux temperature in an argon atmosphere for 2 hours. The reaction mixture was evaporated to dryness in vacuo, the residue was dissolved in 50% aqueous methanol (125 ml), magnesium oxide (1.0 g) and 5% palladium on charcoal (0.400 g) were added and the mixture was hydrogenated at room temperature and atmospheric pressure for 2 hours. A sample withdrawn at this time, after workup, was analyzed by NMR and shown to contain 5-benzoyl-1,2-dihydro-3H-pyrrolo[1,2-a]pyrrole-1,1-dicarboxylic acid as the sodium salt. (This material is, of course, extremely unstable in acid and decarboxylates immediately to the corresponding monocarboxylic acid if acid is added during the analytical process.) The rest of the solution was filtered through celite, the solid filter cake was washed well with methanol and water. Evaporation of most of the methanol was carried out at reduced pressure. The resulting aqueous material was made acidic with 1 N, hydrochloric acid and the product was extracted into ethyl acetate (200 ml). The aqueous phase was further acidified with a few ml of concentrated hydrochloric acid and extracted with an additional quantity (150 ml) of ethyl acetate. The combined organic phases were washed with saturated sodium chloride solution, dried over sodium sulfate and evaporated to dryness to give a colorless solid (1.19 g, 93%) which was homogeneous by TLC. Recrystallization of this material from dichloromethane-hexane gave a first crop (0.699 g) melting point (154–154.5°) corrected and a second crop (0.170 g) melting point (149–151.5°) corrected. A third crop of the product was obtained by treatment of the residue obtained by evaporation of the mother liquors with activated charcoal in ethyl-acetate. Recrystallization from methanol-water of the material isolated from the ethyl-acetate gave the third crop (0.038 g) melting point (148°–150°) corrected. An authentic sample prepared by a well established alternative route had melting point (154.5°) corrected. The total crystallized yield of 5-benzoyl,2-dihydro-3H-pyrrolo[1,2-a]pyrrole-1-carboxylic acid was (0.907 g, 71%) based on starting material.

B. Similarly, applying the procedure of A, above, to the compounds listed in part B of Example 3, one obtains:

5-benzoyl-6-n-butyl-1,2-dihydro-3H-pyrrolo[1,2-a]pyrrole-1-carboxylic acid;

5-(4-methylbenzoyl)-6,5-methyl-1,2-dihydro-3H-pyrrolo[1,2-a]-pyrrole-1-carboxylic acid.

5-(3-ethoxycarbonylbenzoyl)-6-ethyl-1,2-dihydro-3H-pyrrolo-[1,2-a]pyrrole-1-carboxylic acid;

5-(2-methoxysulfonylbenzyl)-1,2-dihydro-3H-pyrrolo-[1,2-a]pyrrole-1-carboxylic acid.

C. The compounds listed in Part B of this example are also obtained by applying the procedure of Part A herein to those corresponding chloro compounds listed in Part C of Example 3.

EXAMPLE 5

A. Preparation of 5-benzoyl-7-bromo-1,2-dihydro-3H-pyrrolo[1,2-a]pyrrole-1-carboxylic acid (step 5b)

Dimethyl 5-benzoyl-7-bromo-1,2-dihydro-3H-pyrrolo-[1,2-a]pyrrole-1,1-dicarboxylate (2.04 g, 5.0 m moles) was dissolved in methanol (100 ml), and sodium hydroxide (0.40 g, 10 mmoles) was added. This solution as heated at reflux temperature in an argon atmosphere for 2 hours. Evaporation of most of the methanol was carried out at reduced pressure. The resulting aqueous material was made acidic with 1 N, hydrochloric acid and the product was extracted into ethyl acetate (200 ml). The aqueous phase was further acidified with a few ml of concentrated hydrochloric acid and extracted with an additional quantity (150 ml) of ethyl acetate. The combined organic phases were washed with saturated sodium chloride solution, dried over sodium sulfate and evaporated to dryness to give a colorless solid. Recrystallization of this material from dichloromethane-hexane gave 1.34% (80% yield) of material which had characteristics consistent with those of 5-benzoyl-7-bromo-1,2-dihydro-3H-pyrrolo[1,2-a]pyrrole-1-carboxylic acid:

mp: (AcOEt-Hex) 177°–178° (dec). UV: (MeOH) 210, 248.5, 318 nm ($\epsilon$ 8320, 7780, 14,450).

IR: (KBr) 1720, 1630, 1600, 1575 cm$^{-1}$.

NMR: (CDCl$_3$+DMSOd$_6$) 2.60–3.10 (m, 2H) 2.88 (dd, 1H, $J_{AX}$=6 Hz, $J_{BX}$=7 Hz), 4.33–4.67 (m, 2H), 6.70 (s, 1H), 7.33–7.87 (m, 5H).

Calcd. for : C$_{15}$H$_{12}$BrNO$_3$: C, 53.91; H, 3.62; Br, 23.92; N, 4.19. Found: C, 53.78; H, 3.65; Br, 23.89; N, 4.04.

B. In a similar fashion, applying the procedure of part A, above, to the compounds listed in Part B of example 3, one obtains, respectively 5-benzoyl-6-n-butyl-7-bromo-1,2-dihydro-3H-pyrrolo [1,2-a]-pyrrole-1-carboxylic acid;

5-(4-methylbenzoyl)-6-methyl-7-bromo-1,2-dihydro-3H-pyrrolo[1,2-a]-pyrrole-1-carboxylic acid;

5-(3-ethoxycarbonylbenzoyl)-6-ethyl-7-bromo-1,2-dihydro-3H-pyrrolo-[1,2-a]pyrrole-1-carboxylic acid;

5-(2-methoxysulfonyl)-7-bromo-1,2-dihydro-3H-pyrrolo-[1,2-a]pyrrole-1-carboxylic acid.

C. Similarly applying the procedure of Part A, above to the compounds listed in Part C of example 3, one obtains 5-benzoyl-7-chloro-1,2-dihydro-3H-pyrrolo[1,2-a]-pyrrole-1-carboxylic acid;

5-benzoyl-6-n-butyl-7-chloro-1,2-dihydro-3H-pyrrolo-[1,2-a]-pyrrole-1-carboxylic acid;

5-(4-methylbenzoyl)-6-methyl-7-chloro-1,2-dihydro-3H-pyrrolo[1,2-a]-pyrrole-1-carboxylic acid;

5-(3-ethoxycarbonylbenzoyl)-6-ethyl-7-chloro-1,2-dihydro-3H-pyrrolo-[1,2-a]pyrrole-1-carboxylic acid;

5-(2-methoxysulfonylbenzyl)-7-chloro-1,2-dihydro-3H-pyrrolo[1,2-a]pyrrole-1-carboxylic acid.

EXAMPLE 6

Conversion of Free Carboxylic Acid to the Ester

A. A solution of 1.34 g. of 5-benzoyl-7-bromo-1,2-dihydro- 3H-pyrrolo[1,2-a]pyrrole-1-carboxylic acid in 50 ml. of isopropanol, cooled in an ice bath is saturated with gaseous hydrogen chloride, maintaining the temperature of the reaction mixture below 50° C. The ice bath is then removed and the reaction mixture is stirred for 1.5 hours at room temperature, and evaporated to dryness under reduced pressure; 10 ml. of benzene is added to the residue and the solution is evaporated under vacuum once again, repeating this process a total of three times to completely remove the excess hydrogen chloride, thus obtaining of isopropyl 5-benzoyl-7-bromo-1,2-dihydro-3H-pyrrolo[1,2-a]pyrrole-1-carboxylate. The product is recrystallized from methanol-ethyl acetate.

In a similar manner but substituting methanol, n-hexanol, n-heptanol and n-dodecanol for isopropanol in the above procedure there are respectively obtained:

methyl 5-benzoyl-7-bromo-1,2-dihydro-3H-pyrrolo-[1,2-a]pyrrole-1-carboxylate;

n-hexyl 5-benzoyl-7-bromo-1,2-dihydro-3H-pyrrolo-[1,2-a]pyrrole-1-carboxylate;

n-heptyl 5-benzoyl-7-bromo-1,2-dihydro-3H-pyrrolo-[1,2-a]pyrrole-1-carboxylate; and n-dodecyl 5-benzoyl-7-bromo-1,2-dihydro-3H-pyrrolo-[1,2-a]pyrrole-1-carboxylate.

B. In similar fashion, esters of the carboxylic acids listed in example 4, part B and example 5, part B are also synthesized, respectively methyl, n-hexyl, n-heptyl or n-dodecyl 5-benzoyl-6-n-butyl-1,2-dihydro-3H-pyrrolo[1,2-a]pyrrole-1-carboxylate;

methyl, n-hexyl, n-heptyl or n-dodecyl 5-(4-methyl-benzoyl)-6-methyl-1,2-dihydro-3H-pyrrolo[1,2-a]pyrrole-1-carboxylate;

methyl, n-hexyl, n-heptyl or n-dodecyl 5-(3-ethoxycarbonylbenzoyl)-6-ethyl-1,2-dihydro-3H-pyrrolo[1,2-a]-pyrrole-1-carboxylate;

methyl, n-hexyl, n-heptyl or n-dodecyl 5-(2-methoxysulfonyl-benzoyl)-1,2-dihydro-3H-pyrrolo[1,2-a]pyrrole-1-carboxylate;

and methyl, n-hexyl, n-heptyl or n-dodecyl 5-benzoyl-6-n-butyl-7-bromo-1,2-dihydro-3H-pyrrolo[1,2-a]pyrrole-1-carboxylate;

methyl, n-hexyl, n-heptyl or n-dodecyl 5-(4-methylbenzoyl)-6-methyl-7-bromo-1,2-dihydro-3H-pyrrolo[1,2-a]-pyrrole-1-carboxylate;

methyl, n-hexyl, n-heptyl or n-dodecyl 5-(3-ethoxycarbonylbenzoyl)-6-ethyl-7-bromo-1,2-dihydro-3H-pyrrolo-[1,2-a]pyrrole-1-carboxylate;

methyl, n-hexyl, n-heptyl or n-dodecyl 5-(2-methoxysulfonylbenzoyl)-7-bromo-1,2-dihydro-3H-pyrrolo[1,2-a]-pyrrole-1-carboxylate.

C. Using as substrate in the procedure of Part A herein, the compounds of Example 5, Part C, one obtains the corresponding methyl, n-hexyl, n-heptyl, and n-dodecyl esters.

EXAMPLE 7

Preparation of Methyl
5-benzoyl-6,7-dibromo-1,2-dihydro-3H-pyrrol[1,2-a]-
pyrrole-1-carboxylate by direct bromination A: A solution of bromine in acetic acid (2.31 ml containing 0.405 g bromine/ml, i.e., 5.86 mmol) was added slowly and with stirring to methyl 5-benzoyl-1,2-dihydro-3H-pyrrol[1,2-a]pyrrole-1-carboxylate (0.790 g, 2.93 mmol) in acetic acid (6 ml). After five minutes, the reaction mixture was poured into water (80 ml) and the product was extracted into dichloromethane (3×30 ml). The extract was washed with water (3×30 ml), dried over sodium sulfate and evaporated in vacuo. The residue was subjected to TLC on silica gel using dichloromethane-ethyl acetate (97:3) as the developing solvent. The dibromo compound, methyl 5-benzoyl-6,7-dibromo-1,2-dihydro-3H-pyrrol[1,2-a]-pyrrole-1-carboxylate (1.12 g, 90%) was crystallized from dichloromethane-methanol with the characteristics:

m.p. ($CH_2Cl_2$—MeOH) 130.5°–131.5°.

UV: (MeOH) 210, 246.5, 312 nm ($\epsilon$ 10,700, 8300 13,200).

IR: ($CHCl_3$) 1745, 1735, 1625, 1600, 1580 (cm$^{-1}$.

NMR: ($CDCl_3$) 2.50–3.03 (m, 2H), 3.75 (s, 3H), 4.00 (dd, 1H, $J_{AX}$=6 Hz, $J_{BX}$- 7 Hz), 4.20–4.60 (m, 2H), 7.20–7.85 (m, 5H).

Calcd. for $C_{16}H_{13}Br_2NO_3$: C, 44.99; H, 3.07: Br, 37.42; N, 3.28. Found: C, 44.84; H, 2.96; Br, 37.31; N, 3.20.

B. In a similar manner, using as substrate material
methyl 5-(4-methylbenzoyl)-1,2-dihydro-3H-pyrrolo[1,2-a]pyrrole-1-carboxylate;
methyl 5-(3-ethoxycarbonylbenzoyl)-1,2-dihydro-3H-pyrrolo[1,2-a]pyrrole-1-carboxylate;
methyl 5-(3-methoxysulfonylbenzoyl)-1,2-dihydro-3H-pyrrolo[1,2-a[pyrrole-1-carboxylate;
methyl 5-(4-fluorobenzoyl)-1,2-dihydro-3H-pyrrolo[1,2-a]pyrrole-1-carboxylate;
methyl 5-(2-bromobenzoyl)-1,2-dihydro-3H-pyrrolo[1,2-a]pyrrole-1-carboxylate; one obtains the corresponding
methyl 5-(4-methylbenzoyl)-6,7-dibromo-1,2-dihydro-3H-pyrrolo[1,2-a]pyrrole-1-carboxylate;
methyl 5-(3-ethoxybenzoyl)-6,7-dibromo-1,2-dihydro3H-pyrrolo[1,2-a]pyrrole-1-carboxylate;
methyl 5-(3-methoxysulfonylbenzoyl)-6,7-dibromo-1,2-dihydro-3H-pyrrolo[1,2-a]pyrrole-1-carboxylate;
methyl 5-(4-fluorobenzoyl)-6,7-dibromo-1,2-dihydro-3H-pyrrolo[1,2-a]pyrrole-1-carboxylate;
methyl 5-(2-bromobenzoyl)-6,7-dibromo-1,2-dihydro-3H-pyrrolo[1,2-a]pyrrole-1-carboxylate.

EXAMPLE 8

Preparation of
5-Benzoyl-6,7-Dibromo-1,1-dihydro-3H-pyrrolo[1,2-a]pyrrole-1-carboxylic acid by Hydrolysis of the Ester A. The dibromo ester of Example 8, part A (1.02 g, 2.39 mmol) dissolved in methanol (15 ml) containing anhydrous potassium carbonate (0.280 g, 7.17 mmol) and water (5 ml) was heated at reflux temperature for 20 min. The solvent was removed in vacuo, water (50 ml) was added to the residue and the resulting solution was extracted with ethyl acetate (60 ml). The aqueous phase was made acidic with oxalic acid (3.3 g) dissolved in water (20 ml) and the product was extracted into ethyl acetate (3×70 ml). The extract was washed with a saturated sodium potassium tartarate solution (3×230 ml) and then with magnesium sulfate and evaporated at reduced pressure. The residue 5-benzoyl-6,7-dibromo-1,1-dihydro-3H-pyrrolo[1,2-a]pyrrole-1-carboxylic acid (0.940 g, 95% was crystallized from ethyl acetate.

mp: (AcOEt) 221°–222° (dec).

UV: (MeOH) 209.5, 256, 314 nm ($\epsilon$10,500, 7600, 12,300).

IR: (KBr) 1720, 1625, 1600, 1590 cm$^{-1}$.

NMR: ($CDCl_3$+$DMSOd_6$) 2.50–3.00 (m, 2H), 3.95 (dd, 1H, $J_{AX}$=6 Hz, $J_{BX-}$7 Hz), 4.17–4.53 (m, 2H), 7.30–7.83 (m, 5H), 10.17 (s, (br), 1H).

Calc. for $C_{15}H_{11}Br_2NO_3$: C, 43.61; H, 2.69; Br, 38.69; N, 3.39. Found: C, 43.69; H, 2.59; Br, 38.64; N, 3.33.

B. In a similar manner, using the compounds prepared in Example 7 part B as substrates, one obtains the corresponding products:
5-(4-methylbenzoyl)-6,7-dibromo-1,2-dihydro-3H-pyrrolo[1,2-a]pyrrole-1-carboxylic acid;
5-(3-ethoxycarbonylbenzoyl)-6,7-dibromo-1,2-dihydro-3H-pyrrolo[1,2-a]pyrrole-1-carboxylic acid;
5-(3-methoxysulfonylbenzoyl)-6,7-dibromo-1,2-dihydro-3H-pyrrolo[1,2-a]pyrrole-1-carboxylic acid;
5-(4-flurobenzoyl)-6,7-dibromo-1,2-dihydro-3H-pyrrolo[1,2-a]pyrrole-1-carboxylic acid;
5-(2-bromobenzoyl)-6,7-dibromo-1,2-dihydro-3H-pyrrolo[1,2-a]pyrrole-1-carboxylic acid.

EXAMPLE 9

Preparation of Methyl
5-benzoyl-7-bromo-1,2-dihydro-3H-pyrrolo[1,2-a]pyrrole-1-carboxylate A. A solution of bromine in acetic acid (0.985 ml of a solution containing 0.235 g bromine/ml, i.e., 2 mmol) was added slowly to a solution of methyl 5-benzoyl-1,2-dihydro-3H-pyrrolo[1,2-a]pyrrole-1-carboxylate (0.540 g, 2 mmol) in acetic acid (3 ml). After 5 minutes, water (30 ml) was added and the product was extracted into dichloromethane (3×50 ml). The extract was washed with water, dried over sodium sulfate and evaporated in vacuo. The residue was purified by TLC on silica gel using dichloromethane-ethyl acetate (97.5:2.5) as the developing solvent. There was thus obtained a small amount of the dibromo ester (0.052 g, 6%) and the monobromo ester (0.610 g, 86.5%) methyl 5-benzoyl-7-bromo-1,2-dihydro-3H-pyrrolo[1,2-a]-pyrrole-1-carboxylate. The latter was crystallized from methanol, mp: (MeOH) 88°–89°.

UV: (MeOH) 210, 249, 314.5 nm ($\epsilon$8700, 7600, 15,200).

IR: (KBr) 1730, 1625, 1575, cm$^{-1}$.

NMR: ($CDCl_3$) 2.57–3.05 (m, 2H), 3.77 (s, 3H), 3.98 (dd, 1H, $J_{AX}$=7 Hz, $J_{BX}$=7 Hz), 4.27–4.70 (m, 2H), 6.73 (s, 1H), 7.30–7.90 (m, 5H).

Anal. Calcd. for $C_{16}H_{14}BrNO_3$: C, 55.19; H, 4.05; Br, 22.95; N, 4.02. Found: C, 55.13; H, 4.10; Br, 22.71; N, 3.92.

B. Similarly, using as substrate in the procedure of part A
methyl 5-(4-methylbenzoyl)-1,2-dihydro-3H-pyrrolo-[1,2-a]pyrrole-1 carboxylate;
methyl 5-(3-ethoxycarbonylbenzoyl)-1,2-dihydro-3H-pyrrolo-[1,2-a]pyrrole-1-carboxylate;
methyl 5-(3-methoxysulfonylbenzoyl)-1,2-dihydro-3H-pyrrolo-[1,2-a]pyrrole-1-carboxylate;
methyl 5-(4-fluorobenzoyl)-1,2-dihydro-3H-pyrrolo-[1,2-a]pyrrole-1-carboxylate;

methyl 5-(2-bromobenzoyl)-1,2-dihydro-3H-pyrrolo-[1,2-a]pyrrole-1-carboxylate;
methyl 5-(4-methylbenzoyl)-6-methyl-1,2-dihydro-3H-pyrrolo-[1,2-a]pyrrole-1-carboxylate;
methyl 5-(4-methylbenzoyl)-6-n-butyl-1,2-dihydro-3H-pyrrolo-[1,2-a]pyrrole-1-carboxylate;
methyl 5-benzoyl-6-methyl-1,2-dihydro-3H-pyrrolo-[1,2-a]pyrrole-1-carboxylate;
methyl 5-benzoyl-6-n-butyl-1,2-dihydro-3H-pyrrolo-[1,2-a]pyrrole-1-carboxylate; one obtains
methyl 5-(4-methylbenzoyl)-7-bromo-1,2-dihydro-3H-pyrrolo-[1,2-a]pyrrole-1-carboxylate;
methyl 5-(3-ethoxycarbonylbenzoyl)-7-bromo-1,2-dihydro-3H-pyrrolo[1,2-a]pyrrole-1-carboxylate;
methyl 5-(3-methoxysulfonylbenzoyl)-7-bromo-1,2-dihydro-3H-pyrrolo[1,2-a]pyrrole-1-carboxylate;
methyl 5-(4-fluorobenzoyl)-7-bromo-1,2-dihydro-3H-pyrrolo[1,2-a]pyrrole-1-carboxylate;
methyl 5-(2-bromobenzoyl)-7-bromo-1,2-dihydro-3H-pyrrolo[1,2-a]pyrrole-1-carboxylate;
methyl 5-(4-methylbenzoyl)-6-methyl-7-bromo-1,2-dihydro-3H-pyrrolo[1,2-a]pyrrole-1-carboxylate;
methyl 5-(4-methylbenzoyl)-6-n-butyl-7-bromo-1,2-dihydro-3H-pyrrolo[1,2-a]pyrrole-1-carboxylate;
methyl 5-benzoyl-6-methyl-7-bromo-1,2-dihydro-3H-pyrrolo[1,2-a]pyrrole-1 carboxylate;
methyl 5-benzoyl-6-n-butyl-7-bromo-1,2-dihydro-3H-pyrrolo[1,2-a]pyrrole-1carboxylate.

EXAMPLE 10

Preparation of
5-Benzoyl-7-bromo-a,2-dihydro-3H-pyrrolo[1,2-a]pyrrole-1-carboxylic acid A. A solution of methyl 5-benzoyl-1,2-dihydro-3H-pyrrole[1,2-a]pyrrole-1-carboxylate (0,750 g, 2.26 mmol) in methanol (20 ml) containing potassium carbonate (0.600 g, 4.32 mmol) and water (5 ml) was heated at reflux temperature in an argon atmosphere for 20 min. The solvent was removed in vacuo and water (20 ml) and oxalic acid (2.18 g, 17.3 mmol) in water (20 ml) were added. The mixture was extracted with ethyl acetate (3×20 ml), the extract was dried over sodium sulfate and evaporated in vacuo. The residue, 5-benzoyl-7-bromo-1,2-dihydro-3H-pyrrolo[1,2-a]pyrrole-1-carboxylic acid (0.650 g, 90%) was crystallized from ethyl acetatehexane.

mp: (AcOEt-Hex) 177°–178° (dec).
UV: (MeOH) 210, 248.5, 318 nm ($\epsilon$8320, 7780, 14,450).
IR: (KBr) 1720, 1630, 1600, 1575 cm$^{-1}$.
NMR: (CDCl$_3$+DMSOd$_6$) 2.60–3.10 (m, 2H), 2.88 (dd, 1H, $J_{AX}$=6 Hz $J_{BX}$=7 Hz), 4.33–4.67 (m, 2H), 6.70 (s, 1H), 7.33–7.87 (m, 5H).
Calcd. for C$_{15}$H$_{12}$BrNO$_3$: C, 53.91; H, 3.62; Br, 23.92; N, 4.19. Found: C, 53.78; H, 3.65; Br, 23.89; N, 4.04.

B. Similarly, using as substrates in the procedure of part A above, the esters obtained in Example 9, part B, one obtains:
5-(4-methylbenzoyl)-7-bromo-1,2-dihydro-3H-pyrrolo-[1,2-a]pyrrole-1-carboxylic acid;
5-(3-ethoxycarbonylbenzoyl)-7-bromo-1,2-dihydro-3H-pyrrolo-[1,2-a]pyrrole-1-carboxylic acid;
5-(3-methoxysulfonylbenzoyl)7-bromo-1,2-dihydro-3H-pyrrolo[1,2-a]pyrrole-1-carboxylic acid;
5-(4-fluorobenzoyl)-7-bromo-1,2-dihydro-3H-pyrrolo-[1,2-a]pyrrole-1-carboxylic acid;
5-(2-bromobenzoyl)-7-bromo-1,2-dihydro-3H-pyrrolo-[1,2-a]pyrrole-1-carboxylic acid;
1-6-methyl-7-bromo-1,2-dihydro-3H-pyrrolo[1,2-a]pyrrole-1-carboxylic acid;
1-6-n-butyl-7-bromo-1,2-dihydro-3H-pyrrolo[1,2-a]pyrrole-1-carboxylic acid;
5-benzoyl-6-methyl 7-bromo-1,2-dihydro-3H-pyrrolo-[1,2-a]pyrrole-1-carboxylic acid;
5-benzoyl-6-n-butyl-7-bromo-1,2-dihydro-3H-pyrrolo-[1,2-a]pyrrole-1-carboxylic acid.

EXAMPLE 11

Preparation of Methyl
5-benzoyl-6,7-dichloro-1,2-dihydro-3H-pyrrolo[1,2-a]pyrrole-1-carboxylate and Methyl
5-benzoyl-7-chloro-1,2-dihydro-3H-pyrrole[1,2-a]pyrrole-1-carboxylate A. A solution of chlorine in chloroform (5.5 ml of solution containing 0.0258 g chlorine/ml, i.e., 2.0 mmol) was added with stirring to a mixture of methyl 5-benzoyl-1,2-dihydro-3H-pyrrole[1.2.a]pyrrole-1-carboxylate (0.5385 g, 2 mmol), calcium carbonate (0.40 g, 4 mmol), ferric chloride (0.010 g) and chloroform (5 ml) in an argon atmosphere. After 1 hour the mixture was filtered, the filtrate was evaporated at reduced pressure and the residue was separated by TLC on silica gel using dichloromethane-ethyl acetate (97:3) as the developing solvent. There was thus obtained the dichloro compound (28%), the mono chloro compound (5%) and starting material (50%).

For methyl 5-benzoyl-6,7-dichloro-1,2-dihydro-3H-pyrrolo[1,2-a]pyrrole-1-carboxylate
mp: oil.
UV: (MeOH) 213.5, 256, 311 nm ($\epsilon$7250, 6600, 10,500).
IR: CHC13) 1745, 1625, 1600, 1580 cm$^{-1}$.
NMR: (CDC$_3$) 2.50–3.05 (m, 2H), 3.77 (s, 3H), 4.07 (dd, 1H, $J_{AX}$=6 Hz, $J_{BX}$=7 Hz), 4.25–4.65 (m, 2H), 7.30–7.85 (m, 5H).

For methyl 5-benzoyl-7-chloro-12-dihydro-3H-pyrrolo[1,2-a]pyrrole-1-carboxylate
mp: oil.
UV: (MeOH) 209, 249.5, 313.5 nm ($\epsilon$8700, 7600, 14,800).
IR: (CHCl$_3$) 1740, 1625, 1580, cm$^{-1}$.
NMR: (CDCl$_3$) 2.60–3.05 (m, 2H), 3.73 (s, 3H), 4.00 (dd, 1H, $J_{AX}$=6 Hz, $J_{BX}$=7 Hz), 4.30–4.68 (m, 2H), 6.72 (s, 1H), 7.27=7.87 (m, 5H).
MS: M+(303–305).

B. In like manner, applying the procedure of Part A, above to
methyl 5-(4-methylbenzoyl)-1,2-dihydro-3H-pyrrolo-[1,2-a]-pyrrole-1-carboxylate;
methyl 5-(3-ethoxycarbonylbenzoyl)-1,2-dihydro-3H-pyrrolo-[1,2-a]-pyrrole-1-carboxylate;
methyl 5-(3-methoxysurfonylbenzoyl)-1,2-dihydro-3H-pyrrolo-[1,2-a]pyrrole-1-carboxylate;
methyl 5-(4-fluorobenzoyl)-1,2-dihydro-3H-pyrrolo-[1,2-a]pyrrole-1-carboxylate;
methyl 5-(2-bromobenzoyl)-1,2-dihydro-3H-pyrrolo-[1,2-a]pyrrole-1-carboxylate;
one obtains similar mixtures containing
methyl 5-(4-methylbenzoyl)-6,7-dichloro-1,2-dihydro-3H-pyrrolo[1,2-a]pyrrole-1-carboxylate and methyl 5-(4-methylbenzoyl)-7-chloro-1,2-dihydro-3H-pyrrolo[1,2-a]pyrrole-1-carboxylate;
methyl 5-(3-ethoxycarbonylbenzoyl)-6,7-dichloro-1,2-dihydro-3H-pyrrolo[1,2-a]pyrrole-1-carboxylate and methyl 5-(3-ethoxycarbonylbenzoyl)-7-chloro-1,2-dihydro-3H pyrrolo[1,2-a]pyrrole-1-carboxylate;

methyl 5-(3-methoxysulfonylbenzoyl)-6,7-dichloro-1,2-dihydro-3H-pyrrolo-[1,2-a]pyrrole-1-carboxylate and methyl 5-(3-methoxysulfonylbenzoyl)-7-chloro-1,2-dihydro-3H pyrrolo[1,2-a]pyrrole-1-carboxylate;

methyl 5-(4-fluorobenzoyl)-6,7-dichloro-1,2-dihydro-3H-pyrrolo[1,2-a]pyrrole-1-carboxylate and methyl 5-(4-fluorobenzoyl)-7-chloro-1,2-dihydro-3H-pyrrolo-8 1,2-a]pyrrole-1-carboxylate;

methyl 5-(2-bromobenzoyl)-6,7-dichloro-1,2-dihydro-3H-pyrrolo[1,2-a]pyrrole-1-carboxylate and methyl 5-(2-bromobenzoyl)-7-chloro-1,2-dihydro-3H-pyrrolo[1,2-a]pyrrole-1-carboxylate.

C. In like manner, applying the procedure of part A above to methyl 5-(4-methylbenzoyl)-6-methyl-1,2-dihydro-3H-pyrrolo[1,2-a]pyrrole-1-carboxylate;

methyl 5-(4-methylbenzoyl)-6-n-butyl,-1,2-dihydro-3H-pyrrolo[1,2-a]pyrrole-1-carboxylate;

methyl 5-benzoyl-6-methyl-1,2-dihydro-3H-pyrrolo-[1,2-a]pyrrole-1-carboxylate;

methyl 5-benzoyl-6-n-butyl-1,2-dihydro-3H-pyrrolo-[1,2-a]pyrrole-1-carboxylate;

one obtains exclusively the 7 chloro derivatives:

methyl 5-(4-methylbenzoyl)-6-methyl-7-chloro-1,2-dihydro-3H-pyrrolo[1,2-a]pyrrole-1-carboxylate;

methyl 5-(4methylbenzoyl)-6-n-butyl-7-chloro-1,2-dihydro-3H-pyrrolo[1,2-a]pyrrole-1-carboxylate;

methyl 5-benzoyl-6-methyl-7-chloro-1,2-dihydro-3H-pyrrolo[1,2-a]pyrrole-1-carboxylate;

methyl 5-benzoyl-6-n-butyl-7-chloro-1,2-dihydro-3H-pyrrolo[1,2-a]pyrrole-1-carboxylate.

EXAMPLE 12

Preparation of 5-Benzoyl-6,7-dichloro-1,2-dihydro-3H-pyrrolo[1,2-a]-pyrrole-1-carboxylic acid and of 5-Benzoyl-7-chloro-1,2-dihydro-3H-pyrrolo[1,2-a]pyrrole-1-carboxylic acid A. Each of the carboxylates in Example 11, part A was hydrolyzed to the corresponding carboxylic acid using anhydrous potassium carbonate in methanol essentially as described in Example 10 herein. For 5-benzoyl-6,7-dichloro-1,2-dihydro-3H-pyrrolo[1,2-a]pyrrole-1-carboxylic acid:

mp: (Et$_2$0) 192°—193°.

UV: (MeOH) 212.5, 255.5, 313 nm ($\epsilon$8130, 7750, 13,200).

IR: (KBr) 1725, 1630, 1600, 1580 cm$^{-1}$.

NMR: (CDCl$_3$+DMSO$_6$) 2.67–3.00 (m, 2H), 4.00 (dd, 1H, J$_{AX}$=6 Hz, J$_{BX}$=7 Hz), 4.23–4.60 (m, 2H), 7.30–7.80 (m, 5H), 8.23 (s (br), 1H).

Calcd. for C$_{15}$H$_{11}$Cl$_2$NO$_3$: C, 55.57; H, 3.42; Cl, 21.88; N, 4.32. Found: C, 55.54; H, 3.47; Cl, 21.66; N, 4.22.

For 5-benzoyl-7-chloro-1,2-dihydro-3H-pyrrolo[1,2-a]pyrrole-1-carboxylic acid:

mp: (Et$_2$O) 162°–163°.

UV: (MeOH) 209.5, 248, 317 nm ($\epsilon$8900, 7930, 15,500).

NMR: (CDCl$_3$+DMSOd$_6$) 2.60–3.05 (m, 2H), 4.00 (dd, 1H, J$_{AX}$=6 Hz, J$_{BX}$=7 Hz), 4.30–4.67 (m, 2H), 6.62 (s, 1H), 7.30–7.87 (m, 5H), 9.70 (s (br), 1H).

Anal. Calcd. for C$_{15}$H$_{12}$ClNO$_3$: C, 62.18; H, 4.18; Cl, 12.24; N, 4.83. Found: C, 62.09; H, 4.14; Cl, 12.14; N, 4.80.

B. Each of the carboxylates obtained as listed in part B of example 11 is converted to the free carboxylic acid according to the procedure of Part A to yield:

5-(4-methylbenzoyl)-6,7-dichloro-1,2-dihydro-3H-pyrrolo[1,2-a]pyrrole-1-carboxylic acid and 5-(4-methylbenzoyl)-7-chloro-1,2-dihydro-3H-pyrrolo[1,2-a]pyrrole-1-carboxylic acid;

5-(3-ethoxycarbonylbenzoyl)-6,7-dichloro-1,2-dihydro-3H-pyrrolo[1,2-a]pyrrole-1-carboxylic acid and 5-(3-ethoxycarbonylbenzoyl)-7-chloro-1,2-dihydro-3H-pyrrolo[1,2-a]pyrrole-1-carboxylic acid;

5-(3-methoxysulfonylbenzoyl)-6,7-dichloro-1,2-dihydro-3H-pyrrolo[1,2-a]pyrrole-1-carboxylic acid and 5-(3-methoxysulfonylbenzoyl)-7-chloro-1,2-dihydro-3H-pyrrolo[1,2-a]pyrrole-1-carboxylic acid;

5-(4-fluorobenzoyl)-6,7-dichloro-1,2-dihydro-3H-pyrrolo[1,2-a]pyrrole-1-carboxylic acid and 5-(4-fluorobenzoyl)-7-chloro-1,2-dihydro-3H-pyrrolo[1,2-a]pyrrole-1-carboxylic acid;

5-(2-bromobenzoyl)-6,7-dichloro-1,2-dihydro-3H-pyrrolo[1,2-a]-pyrrole-1-carboxylic acid and 5-(2-bromobenzoyl)-7-chloro-1,2-dihydro-3H-pyrrolo[1,2-a]-pyrrole-1-carboxylic acid.

C. Each of the carboxylates prepared as listed in part C of Example 11 is converted to the free carboxylic acid according to the procedure of part A to yield:

5-(4-methylbenzoyl)-6-methyl-7-chloro-1,2-dihydro-3H-pyrrolo[1,2-a]pyrrole-1-carboxylic acid;

5-(4-methylbenzoyl)-6-n-butyl-7-chloro-1,2-dihydro-3H-pyrrolo[1,2-a]pyrrole-1-carboxylic acid;

5-benzoyl-6-methyl-7-chloro-1,2-dihydro-3H-pyrrolo[1,2-a]pyrrole-1-carboxylic acid;

5-benzoyl-6-n-butyl-7-chloro-1,2-dihydro-3H-pyrrolo[1,2-a]pyrrole-1-carboxylic acid.

EXAMPLE 13

Conversion of Ester to Free Acid (Basic Conditions)

A: A solution of 336 mg. of isopropyl 5-benzoyl-7-bromo-1,2-dihydro-3H-pyrrolo[1,2-a]-pyrrole-1-carboxylate in 10 ml. of methanol is treated with a solution of 690 mg. of potassium carbonate in 5 ml. of water. The reaction mixture is refluxed under nitrogen atmosphere for 30 minutes, cooled, and evaporated to dryness. The residue is taken up in 10 ml. of 10% aqueous hydrochloric acid and 50 ml. of water and the resultant mixture extracted with ethyl acetate (2×50 ml.). The combined extracts are dried over magnesium sulfate and evaporated to dryness under reduced pressure. Crystallization of the residue from ethyl acetate-hexane affords 5-benzoyl-7-bromo-1,2-dihydro-3H-pyrrolo[1,2-a]pyrrole-1-carboxylic acid.

B. A solution of 250 mg. of ethyl 5-benzoyl-7-bromo-1,2-dihydro-3H-pyrrolo[1,2-a]pyrrole-1-carboxylate in 8 ml. of methanol is treated under an atmosphere of nitrogen, with a solution of 200 mg. of sodium hydroxide in 1 ml. of water, maintaining the reaction mixture at room temperature for 1.5 hours. The methanol is then removed under reduced pressure and the basic solution which remains is diluted with 5 ml. of water and extracted with ether to remove any unsaponifiable product. The aqueous solution is acidified with 10% hydrochloric acid and extracted three times with ethyl acetate. The combined extracts are dried and evaporated to dryness under reduced pressure, and the residue crystallized from ethyl acetate-hexane, to give 5-benzoyl-7-bromo-1,2-dihydro-3H-pyrrolo[1,2-a]pyrrole-1-carboxylic acid.

C. Formation of other acids of the invention.

Following the procedures outlined in parts A and B above, the free acids may be obtained from the esters set forth in Example 6, Part A, B and C.

EXAMPLE 14

Formation of Salts

A. To a solution of 200 mg. of 5-benzoyl-7-bromo-1,2-dihydro-3H-pyrrolo[1,2-a]pyrrole-1-carboxylic acid in 5 ml. of methanol is added 1 molar equivalent of potassium hydroxide in the form of a 0.1 N solution. The solvent is stripped and the residue is dissolved in 5 ml. of water. The thus obtained aqueous solution of potassium 5-benzoyl-7-bromo-1,2-dihydro-3H-pyrrolo[1,2-a]-pyrrole-1-carboxylate is added to a solution of 150 mg. of cupric nitrate trihydrate in 5 ml. of water. The formed precipitate is collected, washed with water and air dried, thus obtaining copper 5-benzoyl-7-bromo-1,2-dihydro-3H-pyrrolo[1,2-a]pyrrole-1-carboxylate.

B. In a similar manner the free acid compounds as set forth in Examnple 8, part B, Example 10, part B and Example 12, part B are converted to their copper salts.

C. A solution containing 200 mg. of 5-benzoyl-7-bromo-1,2-dihydro-3H-pyrrolo[1,2-a]pyrrole-1-carboxylic acid in 15 ml. of hot benzene is treated with 60 mg. of isopropylamine. The solution is allowed to cool to room temperature and the product filtered off, washed with ether and dried to yield the isopropylamine salt of 5-benzoyl-7-bromo-1,2-dihydro-3H-pyrrolo[1,2a]pyrrole-1-carboxylic acid in 15 ml. of hot benzene is treated with 60 mg. of isopropylamine. The solution is allowed to cool to room temperature and the product filtered off, washed with ether and dried to yield the isopropylamine salt of 5-benzoyl-7-bromo-1,2-dihydro-3H-pyrrolo[1,2-a]-pyrrole-1-carboxylic acid.

Likewise other amine salts, e.g., diethylamine, ethanolamine, piperidine, tromethamine, choline and caffeine salts 5-benzoyl-7-bromo-1,2-dihydro-3H-pyrrolo-[1,2-a]pyrrole-1-carboxylic acid are prepared by substituting each of the respective amines for isopropylamine.

D. In similar manner the free acids as set forth in Example 4, Part B, Example 5, Parts B and C, Example 8, Part B, Example 10 part B and Example 12, part B are converted to their isopropylamine, diethylamine, ethanolamine, piperidine, tromethamine, choline and caffeine salts.

E. A solution of 770 mg. of 5-benzoyl-7-bromo-1,2-dihydro-3H-pyrrolo[1,2-a]pyrrole-1-carboxylic acid in 10 ml. of benzene is treated with 580 mg. of dicyclohexylamine. The reaction mixture is stirred for 10 minutes, and the solid which forms is separated by filtration and washed with anhydrous ether thus obtaining 965 mg. of the dicyclohexylammonium salt of 5-benzoyl-7-bromo-1,2-dihydro-3H-pyrrolo[1,2-a]pyrrole-1-carboxylic acid.

F, In similar procedures, free acids as set forth in Example 4, Part B, Example 5, Parts B and C, Example 8, Part B, Example 10, part B and Example 12, part B are converted to their cyclohexyl ammonium salts.

In Examples 15-19, the active ingredient is shown as the free acid, salt or ester of 5-benzoyl-7-bromo-1,2-dihydro-3H-pyrrolo[1,2-a]pyrrole-1-carboxylic acid. Other compounds of formula VI or VII of this invention, in the same status as to acid, salt or ester may, of course, also be used.

EXAMPLE 15

Compositions for oral administration

| (a) Ingredients | Quantity per tablet, mg. |
| --- | --- |
| 5-benzoyl-7-bromo-1,2-dihydro-3H—pyrrolo[1,2-a]pyrrole-1-carboxylic acid | 25 |
| cornstarch | 20 |
| lactose, spray-dried | 153 |
| magnesium stearate | 2 |

The above ingredients are thoroughly mixed and pressed into single scored tablets.

| (b) Ingredients | Quantity per tablet, mg. |
| --- | --- |
| 5-benzoyl-7-bromo-1,2-dihydro-3H—pyrrolo[1,2-a]pyrrole-1-carboxylic acid | 200 |
| cornstarch | 50 |
| lactose | 145 |
| magnesium stearate | 5 |

The above ingredients are mixed intimately and pressed into single scored tablets.

| (c) Ingredients | Quantity per capsule, mg. |
| --- | --- |
| sodium 5-benzoyl-7-bromo-1,2-dihydro-3H—pyrrolo[1,2-a]pyrrole-1-carboxylate | 108 |
| lactose | 15 |
| cornstarch | 25 |
| magnesium stearate | 2 |

The above ingredients are mixed and introduced into a hard-shell gelatin capsule.

| (d) Ingredients | Quantity per capsule, mg. |
| --- | --- |
| calcium 5-benzoyl-7-bromo-1,2-dihydro-3H—pyrrolo[1,2-a]-pyrrole-1-carboxylate | 115 |
| lactose | 93 |
| cornstarch | 40 |
| magnesium stearate | 2 |

The above ingredients are mixed and introduced into a hard-shell gelatin capsule.

| (e) Ingredients | Quantity per tablet, mg. |
| --- | --- |
| isopropylammonium 5-benzoyl-7-bromo-1,2-dihydro-3H—pyrrolo[1,2-a]pyrrole-1-carboxylate | 245 |
| cornstarch | 75 |
| lactose | 175 |
| magnesium stearate | 5 |

The above ingredients are mixed intimately and pressed into single scored tablets.

| (f) Ingredients | Quantity per capsule, mg. |
| --- | --- |
| methyl 5-benzoyl-7-bromo-1,2-dihydro-3H—pyrrolo[1,2-a]pyrrole-1-carboxylate | 25 |

| (f) Ingredients | Quantity per capsule, mg. |
|---|---|
| lactose | 125 |

The above ingredients are mixed and introduced into a No. 1 hard-shell gelatin capsule.

| (g) Ingredients | Quantity per tablet, mg. |
|---|---|
| isoamyl 5-benzoyl-7-bromo-1,2-dihydro-3H—pyrrolo[1,2-a]pyrrole-1-carboxylate | 254 |
| cornstarch | 50 |
| lactose | 190 |
| magnesium stearate | 6 |

The above ingredients are mixed intimately and pressed into single scored tablets.

| (h) Ingredients | Quantity per capsule, mg. |
|---|---|
| 5-benzoyl-7-bromo-1,2-dihydro-3H—pyrrolo[1,2-a]pyrrole-1-carboxylic acid | 100 |
| lactose | 148 |
| dextrose | 2 |

The above ingredients are mixed and introduced into a hard-shell gelatin capsule.

EXAMPLE 16

Composition Suitable for Injection

| | |
|---|---|
| 5-benzoyl-7-bromo-1,2-dihydro-3H—pyrrolo[1,2-a]pyrrole-1-carboxylic acid | 0.2 g |
| $K_2HPO_4$ buffer (0.4 M solution) | 2 ml. |
| KOH (1 N) | qs to pH 7 |
| water (distilled sterile) | qs to 20 ml. |

EXAMPLE 17

Composition for use as a Suppository

A suppository totaling 2.8 grams is prepared having the following composition:

| | |
|---|---|
| 5-benzoyl-7-bromo-1,2-dihydro-3H—pyrrolo[1,2-a]pyrrole-1-carboxylic acid | 25 mg. |
| Witepsol H-15 (triglyceride of saturated vegetable fatty acids; a product of Riches-Nelson, Inc., New York, N.Y.) | balance |

EXAMPLE 18

Pediatric Composition

An oral suspension for pediatric use is prepared having the following composition:

| | |
|---|---|
| 5-benzoyl-7-bromo-1,2-dihydro-3H—pyrrolo[1,2-a]pyrrole-1-carboxylic acid | 0.1 g. |
| fumaric acid | 0.5 g. |
| sodium chloride | 2.0 g. |
| meethyl paraben | 0.1 g. |
| granulated sugar | 25.5 g. |
| sorbitol (70% solution) | 12.85 g. |
| Veegum K (Vanderbilt Co.) | 1.0 g. |
| flavoring | 0.035 ml. |
| colorings | 0.5 mg. |
| distilled water | qs. to 100 ml. |

EXAMPLE 19

Topical Veterinary Composition

Powdered top dressings for veterinary use are prepared having the following compositions:

| | A | B |
|---|---|---|
| 5-benzoyl-7-bromo-1,2-dihydro-3H—pyrrolo[1,2-a]pyrrole-1-carboxylic acid | 0.1 g. | 1.2 g. |
| sucrose | 5.7 g. | 3.7 g. |
| polyvinyl pyrrolidone | 0.3 g. | 0.3 g. |

What is claimed is:

1. A compound of the formula

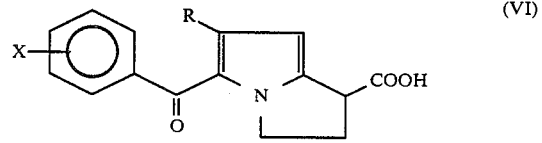

(VI)

wherein

R is hydrogen or lower alkyl;

X is lower alkoxycarbonyl, carboxyl or lower alkylcarbonyl;

and the pharmaceutically acceptable non-toxic estersand salts thereof.

2. A composition for treating inflammation, pain or pyrexia in mammals which comprises an effective amount of the compound of the formula

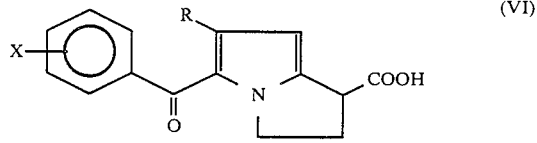

(VI)

wherein

R is hydrogen a lower alkyl; and

X is lower alkoxycarbonyl, carboxyl or lower alkylcarbonyl;

or any of the pharmaceutically acceptable non-toxic esters and salts thereof, as active ingredient, in admixture with a pharmaceutically acceptable non-toxic carrier.

3. A method of treating inflammation, pain or pyrexia in mammals which comprises administering to a subject in need of such treatment, an effective amount of the compound of the formula,

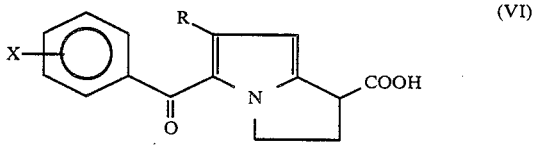

(VI)

wherein
R is hydrogen or lower alkyl; and
X is lower alkoxycarbonyl, carboxyl or lower alkylcarbonyl;
or a pharmaceutically acceptable non-toxic ester or salt thereof, or a pharmaceutical composition containing an effective amount of said compound or a pharmaceutically acceptable non-toxic alkyl ester or salt thereof.

* * * * *